United States Patent [19]
Kasai et al.

[11] Patent Number: 5,098,840
[45] Date of Patent: Mar. 24, 1992

[54] HUMAN PROUROKINASE MUTANTS

[75] Inventors: Shunji Kasai; Ryuji Hiramatsu; Shusei Uno; Masanori Nagai; Hirofumi Arimura; Toshizumi Tanabe; Yasuo Amatsuji; Masaaki Hirose; Masanori Morita; Haruhide Kawabe, all of Osaka, Japan

[73] Assignee: The Green Cross Corporation, Osaka, Japan

[21] Appl. No.: 525,011

[22] Filed: May 18, 1990

Related U.S. Application Data

[63] Continuation-in-part of Ser. No. 70,003, Jul. 6, 1987, abandoned, and a continuation-in-part of Ser. No. 433,938, Nov. 9, 1989, abandoned.

[30] Foreign Application Priority Data

| | | |
|---|---|---|
| Jul. 3, 1986 [JP] | Japan | 61-156936 |
| Feb. 18, 1987 [JP] | Japan | 62-36495 |
| May 18, 1989 [JP] | Japan | 1-126433 |
| May 18, 1989 [JP] | Japan | 1-126434 |
| Feb. 22, 1990 [JP] | Japan | 2-42020 |

[51] Int. Cl.$^5$ .................... C12N 9/72; C12N 15/00
[52] U.S. Cl. ..................... 435/215; 435/172.3; 435/212; 435/226; 435/320.1
[58] Field of Search ............ 435/215, 212, 172.3, 435/320, 226; 536/27; 935/14, 10, 29, 32, 70, 72

[56] References Cited

FOREIGN PATENT DOCUMENTS

| | | |
|---|---|---|
| 0154272 | 2/1985 | European Pat. Off. . |
| 0253241 | 1/1988 | European Pat. Off. . |
| 0266032 | 5/1988 | European Pat. Off. . |
| 0308716 | 3/1989 | European Pat. Off. . |
| 8911531 | 11/1989 | PCT Int'l Appl. . |

OTHER PUBLICATIONS

Cell Structure and Function 10, 151-159 (1985) entitled "Thrombolytic Properties of an Inactive Proenzyme Form of Human Urokinase Secreted from Human Kidney Cells", pp. 151-159.

Hoppe-Seyler's Z. Physiol. Chem. Bd. 363, S.1155-1165, Oct. 1982 entitled "The Primary Structure of High Molecular Mass Urokinase from Human Urine the Complete Amino Acid Sequence of the A Chain".

The Journal of Biological Chemistry, vol. 260, No. 22, Issue of Oct. 5, pp. 12377-12381, 1985 entitled "Proteolytic Cleavage of Single-Chain Pro-Urokinase Induces Conformational Change . . .".

Communication, The Journal of Biological Chemistry, vol. 262, No. 10, Issue of Apr. 5, pp. 4437-4400 4440, 1987 entitled "The Receptor-Binding Sequence of Urokinase"; A Biological Function for the . . . .

Communication, The Journal of Biological Chemistry, vol. 263, No. 4, Issue of Feb. 5, pp. 1599-1602, 1988 entitled "A Tissue-Type Plasminogen Activator Mutant with Prolonged Clearance in vivo"; Effect of Removal of the Growth Factor Domain.

Kornfield et al., Ann. Rev. Biochem., 54, 631-634 (1985).

Primary Examiner—Richard A. Schwartz
Assistant Examiner—Nancy Treptow
Attorney, Agent, or Firm—Sughrue, Mion, Zinn, Macpeack & Seas

[57] ABSTRACT

A human prourokinase mutant in which the entire or a partial epidermal growth factor domain of human prourokinase is deleted or a partial epidermal growth factor domain of human prourokinase is replaced by one or more different amino acid residues, said mutant having a longer blood half-life than naturally occurring human prourokinase while retaining prourokinase enzymatic activity. In this human prourokinase mutant the region selected from the group consisting of: (a) from asparagine (10) to cysteine (42); (b) from asparagine (10) to aspartic acid (45); and (c) from asparagine (10) to threonine (49) is missing.

2 Claims, 12 Drawing Sheets

SJ: SPLICING JUNCTION
SS: SIGNAL SEQUENCE
NC: NON-CODING REGION

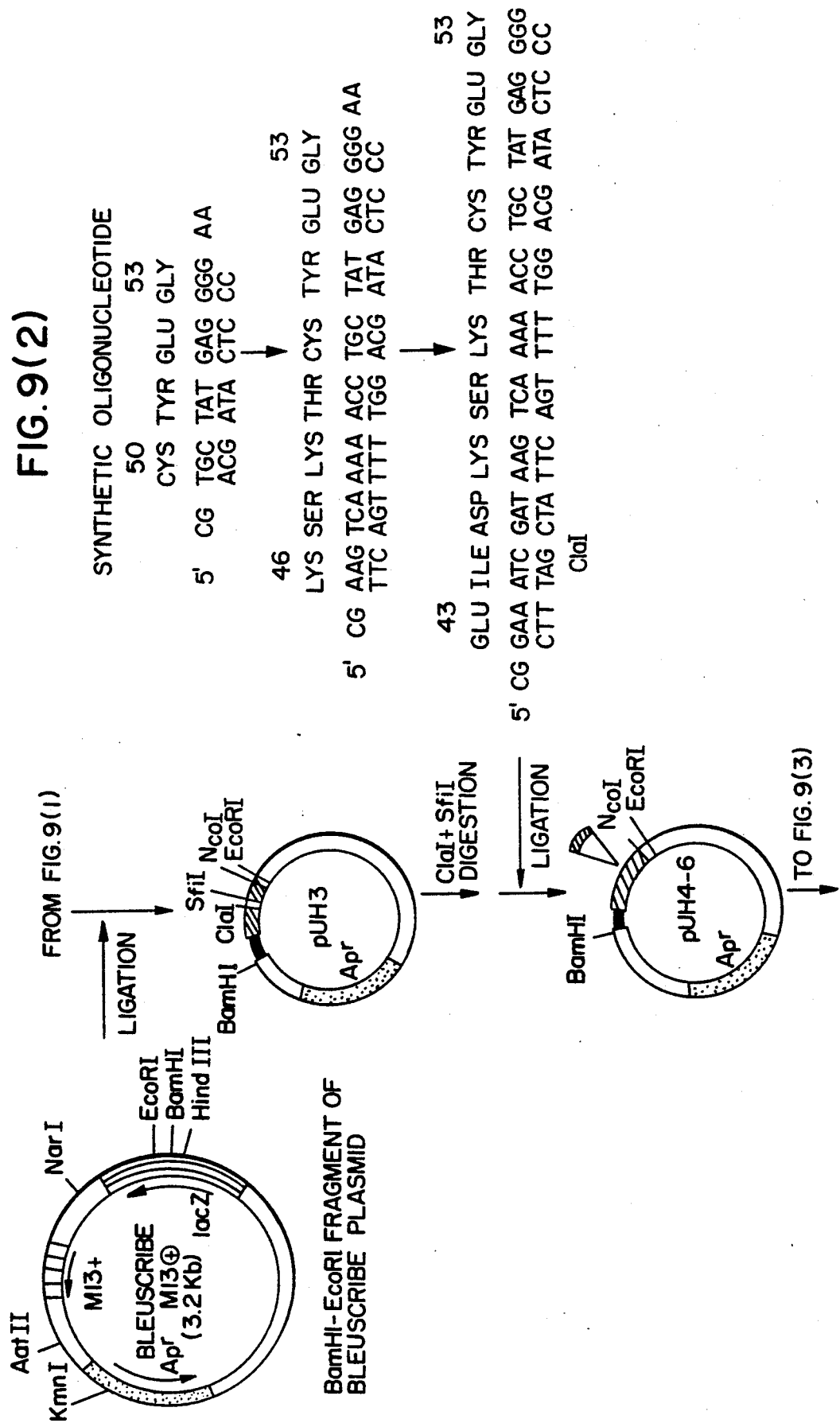

HUMAN PROUROKINASE MUTANTS

RELATED APPLICATIONS

This application is a CIP of U.S. application Ser. No. 07/070,003 filed July 6, 1987, now abandoned, and U.S. application Ser. No. 07/433,938 filed Nov. 9, 1989.

FIELD OF THE INVENTION

This invention relates to mutants or variants of human prourokinase derived from human prourokinase (hereinafter referred to as "human PUK") by modification of its molecular structure, a method of producing the same, DNA sequences coding for the human PUK mutants, plastics containing the DNA sequences inserted therein, and transformants containing the plasmids. More particularly, the invention relates to methods for providing a human PUK mutant by deleting an entire or a partial specific gene region or substituting an entire or a partial specific gene region with one or more different nucleic acid residues, followed by expressing the gene using recombinant DNA techniques.

BACKGROUND OF THE INVENTION

Urokinase is a well-known fibrinolytic enzyme. This enzyme has been purified from human urine and human kidney cell culture fluids. Recently, it has also become possible to produce urokinase using recombinant DNA technology (Japanese Patent Application (OPI) No. 60-180591 corresponding to EP-0154272A and U.S. application Ser. No. 703,678 filed Feb. 15, 1985). However, the thus obtained urokinase has a drawback in that when it is used in large doses, degradation and activation of coagulation and fibrinolysis factors occurs which leads to bleeding. On the other hand, it has been found that an inactive-form (precursor) of human urokinase, namely human PUK, produced by human kidney cells (Japanese Patent Application (OPI) No. 60-62981 (corresponding to EP-0139447A and U.S. application Ser. No. 648,134 filed Sept. 7, 1984): *J. Biol. Chem.*, 260, 12377 (1985), unlike Urokinase, dissolves thrombi without inducing any substantial bleeding (*Cell Struc. Func.*, 10, 151 (1985)).

Human PUK is composed of three functional domains, i.e., (1) the epidermal growth factor (hereinafter abbreviated as "EGF") domain, the (2) kringle domain and (3) the enzyme activity domain (Hoppe-Seyler's Z., Physiol. Chem., 363, 1155 (1982)).

However, this substance, like urokinase, has a drawback in that it has a short half-life in blood. As a result, relatively large doses are required for the purpose of thrombolysis.

SUMMARY OF THE INVENTION

Accordingly, it is an object of the present invention to provide fibrinolytic enzymes having a longer half-life in blood than human PUK and, like human PUK, inducing only a very low level of bleeding: a method of producing the same: DNA sequences coding for the fibrinolytic enzymes: plasmids containing the DNA sequences inserted therein; the transformants containing the plasmids.

The above object of the present invention has been met by recombinant human PUK mutants in which part or all of the EGF domain of human PUK is deleted or substituted by one or more different amino acid residues where these mutants have a longer half-life in blood than that of human PUK but like human PUK. induce only a very low level of bleeding: DNAs coding for the human PUK mutants; plasmids containing the DNA sequences inserted therein; hosts containing the plasmids: and methods of producing the human PUK mutants.

Figure 1:
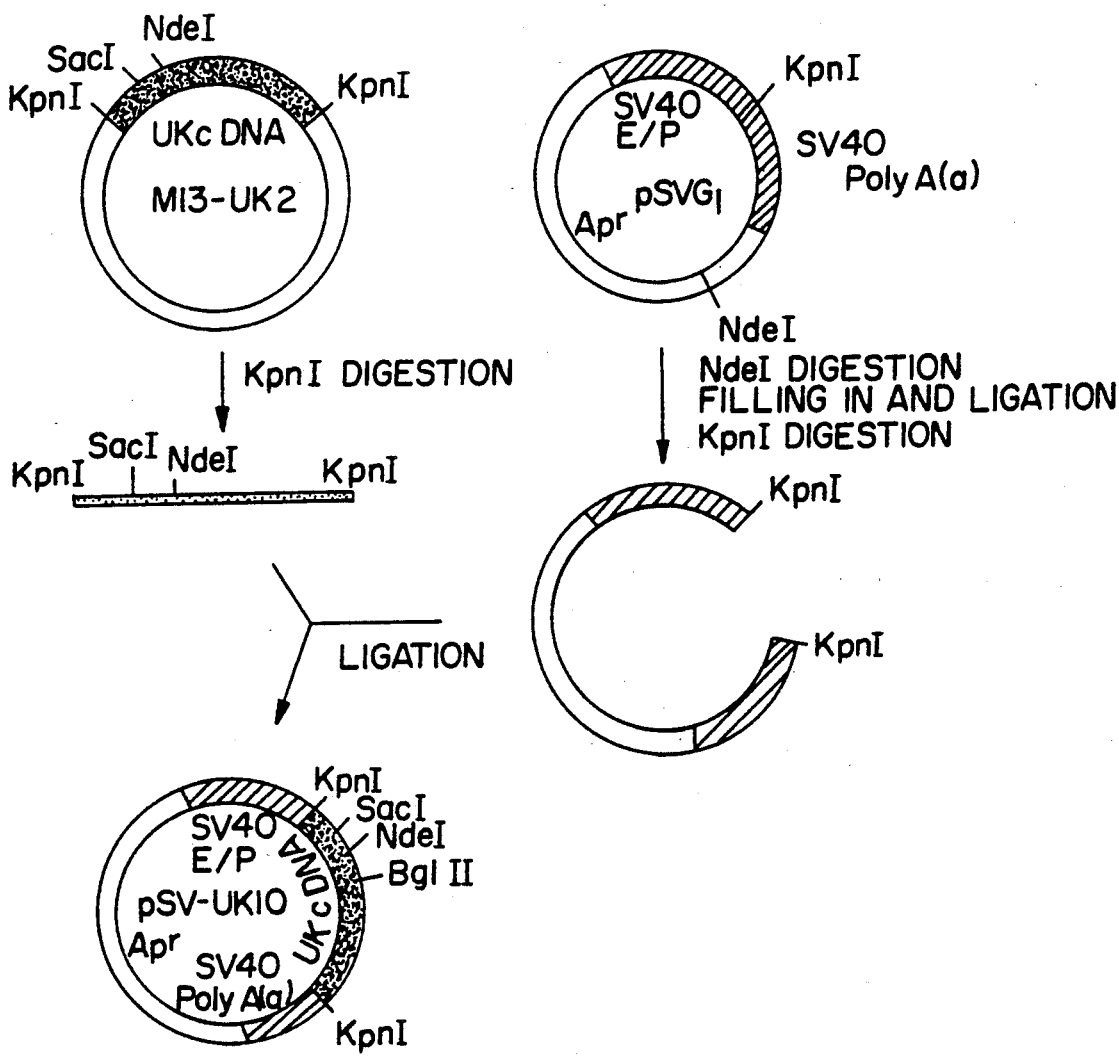
FIG. 1 shows the construction scheme for the human PUK expression vector, pSV-UK10, which has a new restriction enzyme site.

Plasmids pUH7, pUH8 and pUH9 have been deposited via 3 deposits of *E. coli* HB101 at the Institute of Fermentation, Osaka, Japan. The 3 deposits are IFO No. 14636 (pUH7), IFO No. 14637 (pUH8) and IFO No. 14638 (pUH9).

DETAILED DESCRIPTION OF THE INVENTION

It has been reported that among the 411 amino acid residues contained in human PUK, the 49 amino acid residues from the N-terminal serine to the 49th amino acid residue threonine constitute the EGF domain (Riccio. A. et al., *Nucleic Acid Res.*, 13, 2759–2771 (1985)). The EGF domain of PUK includes three loops; Asn(10) to Cys(19) form the first loop. Val(20) to Cys(31) form the second loop and Cys(33) to Cys(42) form the third. Therefore, the present invention provides a method for producing human PUK mutants in which the entire or a partial EGF domain is missing or is substituted by one or more different amino acid residues.

TABLE 1

A portion (A) of the base sequence of human prourokinase cDNA and the base sequence (B) for a human prourokinase mutant designed so as to acquire unique restriction enzyme sites

A

```
-20
MET ARG ALA LEU LEU ALA ARG LEU LEU LEU CYS VAL LEU VAL VAL SER ASP SER LYS GLY
ATG AGA GCC CTG CTG GCG CGC CTG CTT CTC TGC GTC CTG GTC GTG AGC GAC TCC AAA GGC

1                                                                            -1
SER ASN GLU ELU HIS GLN VAL PRO SER ASN CYS ASP CYS LEU ASN GLY GLY THR CYS VAL
AGC AAT GAA CTT CAT CAA GTT CCA TCG AAC TGT GAC TGT CTA AAT GGA GGA ACA TGT GTG
                 ↓
                 G
                 ↓
                 C

21
SER ASN LYS TYR PHE SER ASN ILE HIS TRP CYS ASN CYS PRO LYS LYS PHE GLY CLY GLN
TCC AAC AAG TAC TTC TCC AAC ATT CAC TGG TGC AAC TGC CCA AAG AAA TTC GGA GGG CAG 41                                 50
HIS CYS GLU ILE ASP LYS SER LYS THR CYS TYR GLU GLY ASN GLY HIS PHE TYR ARG GLY
CAC TGT GAA ATA GAT AAG TCA AAA ACC TGC TAT GAG GGG AAT GGT CAC TTT TAC CGA GGA
                            SacI                ↓
                                                CA 61                                                                       80
LYS ALA SER THR ASP THR MET GLY ARG LEU ALA LEU CYS PRO TRP ASN SER ALA THR VAL LEU
ACT GCA TCC ACC GAC ACC ATG GGC CGG CTG GCG CTC TGC CCC TGG AAC TCT GCC ACT GTC CTT
```

B

```
-20
MET ARG ALA LEU LEU ALA ARG LEU LEU LEU CYS VAL LEU VAL VAL SER ASP SER LYS GLY
ATG AGA GCC CTG CTG GCG CGC CTG CTT CTC TGC GTC CTG GTC GTG AGC GAC TCC AAA GGC
----

1                                                                            -1
SER ASN GLU LEU HIS GLN VAL PRO SER ASN CYS ASP CYS LEU ASN GLY GLY THR CYS VAL
AGC AAT GAG CTC CAT CAA GTT CCA TCG AAC TGT GAC TGT CTA AAT GGA GGA ACA TGT GTG
        SacI

21
SER ASN LYS TYR PHE SER ASN ILE HIS TRP CYS ASN CYS PRO LYS LYS PHE GLY GLY GLN
TCC AAC AAG TAC TTC TCC AAC ATT CAC TGG TGC AAC TGC CCA AAG AAA TTC GGA GGG CAG 41                                 50
HIS CYS GLU ILE ASP LYS SER LYS THR (SER) TYR GLU GLY ASN GLY HIS PHE TYR ARG GLY
CAC TGT GAA ATA GAT AAG TCA AAA ACC TCA TAT GAG GGG AAT GGT CAC TTT TAC CGA GGA
                                     NdeI 61                                                                       80
LYS ALA SER THR ASP THR MET GLY ARG LEU PRO CYS LEU TRP ASN SER ALA THR VAL ELU-LYS ALA SER
ACT GAC TCC ACC GAC ACC ATG GGC CGG CTG CCC TGC CTG TGG AAC TCT GCC ACT GTC CTT-
```

As suitable examples of the missing region in the EGF domain-encoding region, the regions from Asn (asparagine) (10) to Cys (cysteine) (42). at least from Asn(10) to Cys(19) (the first loop region) or from Cys(33) to Cys(42) (the third loop region): from Asn (10) to Asp (aspartic acid) (45): and from Asn (10) to Thr (threonine) (49) were selected in preferred embodiments of the invention. The selection was based on the belief that deletion of such regions might result in changes in the three-dimensional structure since the region from Cys (42) to Thr (49) exhibit variable physical properties, namely from hydrophobic to hydrophilic and then again to hydrophobic.

An example of human PUK mutants in which the EGF domain is substituted for by one or more different amino acid residues is a human PUK mutant in which an amino acid sequence (I) occurs in the EGF domain, Asn-X-Y                                                           (I)

wherein X is any amino acid residue and Y is Ser or Thr.

Investigations made by the present inventors have revealed that the half-life in blood of PUK can vary if a carbohydrate chain is bound thereto. Namely, as compared with PUK having no carbohydrate chain, PUK having a complex carbohydrate chain shows long half-life in blood while PUK having a high mannose carbohydrate chain shows short half-life in blood.

The mode of protein-carbohydrate chain bonding includes N-glycosylation and O-glycosylation. Proteins having the amino acid sequence (I) are modified with a carbohydrate chain (N-glycosylation) in the process of their biosynthesis in mammalian cells. Thus, it was suggested that a complex carbohydrate chain is effective because a carbohydrate chain of this type increases the stability of PUK in blood.

In the present invention. X may be a naturally occurring amino acid or a substituted amino acid.

In accordance with the invention, any site in the EGF domain may contain the amino acid sequence (I). Preferably, however, the second loop contains the sequence. Most preferably, Tyr(24) in the second loop is replaced with Ser(24) or Asn(24); or His(29) in the second loop is replaced with Ser(29), with a carbohydrate chain bound to Asn(22), Asn(24) or Asn(27).

For the deletion and substitution of amino acid residue(s), the so-called protein engineering techniques can be widely used, for example, the site-directed deletion technique (Nucl. Acids Res., 11, 1645 (1983)). the site-specific mutagenesis techniques (Craik et al., Science, 228, 291 (1985)). and the technique which employs restriction enzyme treatment and synthetic genes (Wells et al., Gene, 34, 315 (1985)).

Table 1 shows a portion (A) of the base sequence of human prourokinase cDNA prior to the site-specific mutagenesis technique and the base sequence (B) for a human prourokinase mutant obtained by the technique.

The mutant PUK gene resulting from such deletion treatment is inserted into an expression vector system to give a host-vector system for expression. The host-vector system generally comprises the combination of a host and a plasmid vector having a replicon derived from a species compatible with the host cell and a regulatory sequence. The vector generally has a replication site and also has a marker sequence which allows phenotype selection in transformants. For instance, Escherichia coli is transformed generally by using the plasmid pBR322, which is of Escherichia coli strain origin (Bolivar et al., Gene, 2, 95 (1977)). Since it has an ampicillin resistance gene and tetracycline resistance gene. using pBR322 is a simple method of detecting transformants. The pBR322 plasmid and other plasmids such as pBR325, pUC19. pAT153, etc. of microorganism origin have a promoter utilizable by microorganisms to express a protein which is under the control of the promoter or has such a promoter sequence inserted therein.

Examples of promoters which are generally used in constructing such recombinant DNAs include: β-lactamase (penicillinase) or lactose promoters (Chang et al., Nature, 275, 615 (1978): Itakura et al., Science, 198, 1056 (1977); Goeddel et al., Nature, 281, 544 (1979)) and tryptophan (trp) promoters (Goeddel et al. Nucl. Acids Res., 8, 4057 (1979); and European patent application laid open under No. 0036776). While these are most commonly used, other microorganism promoters have been discovered and put into use. The detailed base sequences of these have been published (Siebenlist et al., Cell, 20, 269 (1980); Rosenberg et al., Ann. Rev. Genetics, 13, 19 (1979)). It is well known to functionally introduce such sequences into plasmid vectors (Siebenlist et al., Cell, 20, 269 (1980)). As the host, the well-known Escherichia coli strains HB101-GCC, C600 and W3110 are used, among others.

Suitable examples of the promoters to be used in yeast vectors are the 3-phosphoglycerate kinase (PGK) promoter (Hitzeman et al., Biol. Chem., 255, 2073 (1968) and promoters for other enzymes participating in glycolytic pathway (Hess et al., J. Adv., Enzyme Reg., 7, 149 (1968); Holland et al., Biochemistry, 17, 4900 (1978)), such as enolase, glyceraldehyde-3-phosphate dehydrogenase (GAP-DH), hexokinase, pyruvate decarboxylase, phosphofructokinase, glucose-6-phosphate isomerase, 3-phosphoglycerophosphate mutase, pyruvate kinase, triosephosphate isomerase, phosphoglucose isomerase, and glucokinase. Among these, particularly useful are miniaturized GAP-DH promoters and PGK promoters. In constructing an appropriate expression vector, the transcription terminator occurring in these genes is also inserted on the 3' side of the gene desired to be expressed so that the addition of poly(A) to the mRNA and transcription termination can take place. Promoters capable of advantageously controlling transcription according to growth conditions, such as the promoters for the genes for alcohol dehydrogenase 2, isocytochrome C, acid phosphatase, catabolic enzymes involved in nitrogen metabolism, the above-mentioned glyceraldehyde-3-phosphate dehydrogenase, and enzymes in association with the use of maltose or galactose, may also be used. Plasmid vectors containing a yeast-compatible promoter, a replication origin and a transcription terminator can all be used. As the host, the well-known Saccharomyces cerevisiae strains GRF18 and AH22 are used, among others.

As the secretory expression vector for use in Bacillus subtilis, plasmids having the replication origin of the well-known plasmid pUB110 and having the promoter, signal peptide gene and terminator for the α-amylase gene can be used. Those plasmids containing similar promoter and signal peptide genes as described in Palva et al., Gene, 22, 229 (1983) may also be used. As the host, well-known Bacillus natto as well as well-known Bacillus subtilis can be used, among others.

In recent years, it has become routine to multiply vertebrate animal cells by culture (tissue culture) (Tissue Culture, Academis Press, Kruse and Patterson, editors (1973)). Useful examples of the host cell lines are Vero, HeLa, CHO (Chinese hamster ovary). W138, BHK, COS-7, MDCK, C127, HKG, and human kidney cell lines. The expression vector for use in these cells generally has a replication origin, a promoter located upstream from the gene to be expressed, a ribosome binding site, an RNA splicing site, a poly(A) addition site, and a transcription terminating sequence.

When mammalian cells are used, the regulatory functions on the expression vector are generally of viral origin. For example, the promoters in general use are promoters derived from polyoma, adenovirus 2 or, most frequently, simian virus 40 (SV40). The early and late promoters of SV40 are particularly useful since they can be readily obtained in the form of fragments containing the replication origin of SV40 from the virus (Fiers et al., Nature, 273, 113 (1978)). A fragment of the virus, which comprises about 250 bp from the HindIII site to the BglI site in the replication origin, can be used as well. Furthermore, promoters and regulatory sequences (enhancers) associated with the gene to be expressed can be used provided that they are compatible with the host.

As the promoter-enhancer to be used in expression vectors for use in animal cells, there may be mentioned the SV40 early or late gene promoter-enhancer, the adenovirus major late promoter region, the globulin enhancer-promoter region, the LTR (long terminal repeat) of RNA viruses, the metallothionein promoter region, and the $\beta$-actin promoter, among others. As the replication origin, that of the SV40 origin or of another viral (polyoma, adeno, VSV, BPV, etc.) origin may be incorporated in the vector, or the replication mechanism of the host cell chromosome may be used. The latter is sufficient when the vector is incorporated in the host cell chromosome. In addition, a gene amplification system in which the DHFR gene is utilized can be used as another high production system.

While the present invention has been described hereinabove by giving particular examples, it is to be noted that the invention should by no means be construed as being limited to the host cells, vectors and expression systems mentioned above as examples.

In a preferred embodiment of the invention, expression vectors for use in animal cells were constructed by insertion of a gene coding for a human PUK mutant downstream from the SV40 early promoter region. These vectors were incorporated into COS7 cells or CHOK1 cells to transform them. In this experimental system, clones capable of producing human PUK mutants at a rate of 50–300 IU/ml/day were obtained.

Human PUK mutants can be purified in the same manner as in purifying known human PUK (Japanese Patent Application (OPI) No. 60-62981. In a preferred embodiment of the invention, column chromatography using Chelating Sepharose 6B, anti-UK IgG-Sepharose 4B and p-aminobenzamidine-Sepharose 6B in combination was employed for the purification. Chelating Sepharose 6B is particularly effective in rough purification, anti-UK IgG-Sepharose 4B in high-level purification, and p-aminobenzamidine-Sepharose 6B in removing contaminant active-form urokinase.

Analysis of the thus-obtained product revealed no difference in PUK activity between the mutant form and the non-mutant form. The mutant-form PUK occurred as a single-chain proenzyme having a molecular weight of 45,000 and was completely converted to the active form upon treatment with plasmin. Comparison of the half-life in blood of this human PUK mutant with that of human kidney cell-driven PUK (J. Biol. Chem., 260, 12377 (1985)) showed that the half-life in blood of the mutant human prourokinase was significantly longer.

The following examples are provided for illustrative purposes only and are in no way intended to limit the scope of the present invention.

EXAMPLE 1

(A) Construction of Expression Vector for use in Animal Cells

Figure 2:
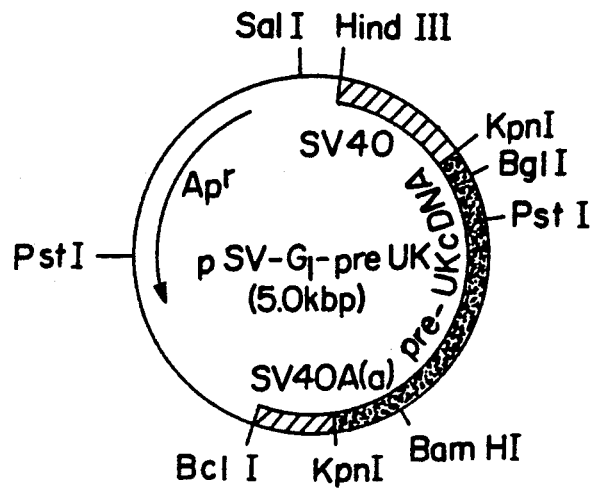
FIG. 2 shows the restriction enzyme map of the human PUK expression, vector, pSV-G$_1$-preUK.
Figure 3:
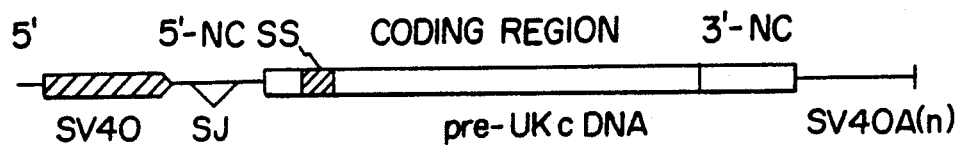
FIG. 3 shows the structure, in the vicinity of the preUK cDNA, of pSV-G$_1$-preUK.

An expression vector, pSV-$G_1$-preUK, allowing efficient secretory production of human PUK, was constructed (FIG. 2). This vector contains a human PUK cDNA inserted downstream from the SV40 early enhancer-promoter region, with the SV40 transcription termination region occurring further downstream from the human PUK cDNA (FIG. 3).

The cloning and sequencing of the PUK cDNA and the construction of the pSV-$G_1$-preUK plasmid were carried out as described in Japanese Patent Application (OPI) No. 60-180591 or EP-154272A.

(B) Insertion of preUK cDNA into M13mp18RF Plasmid

Figure 4:
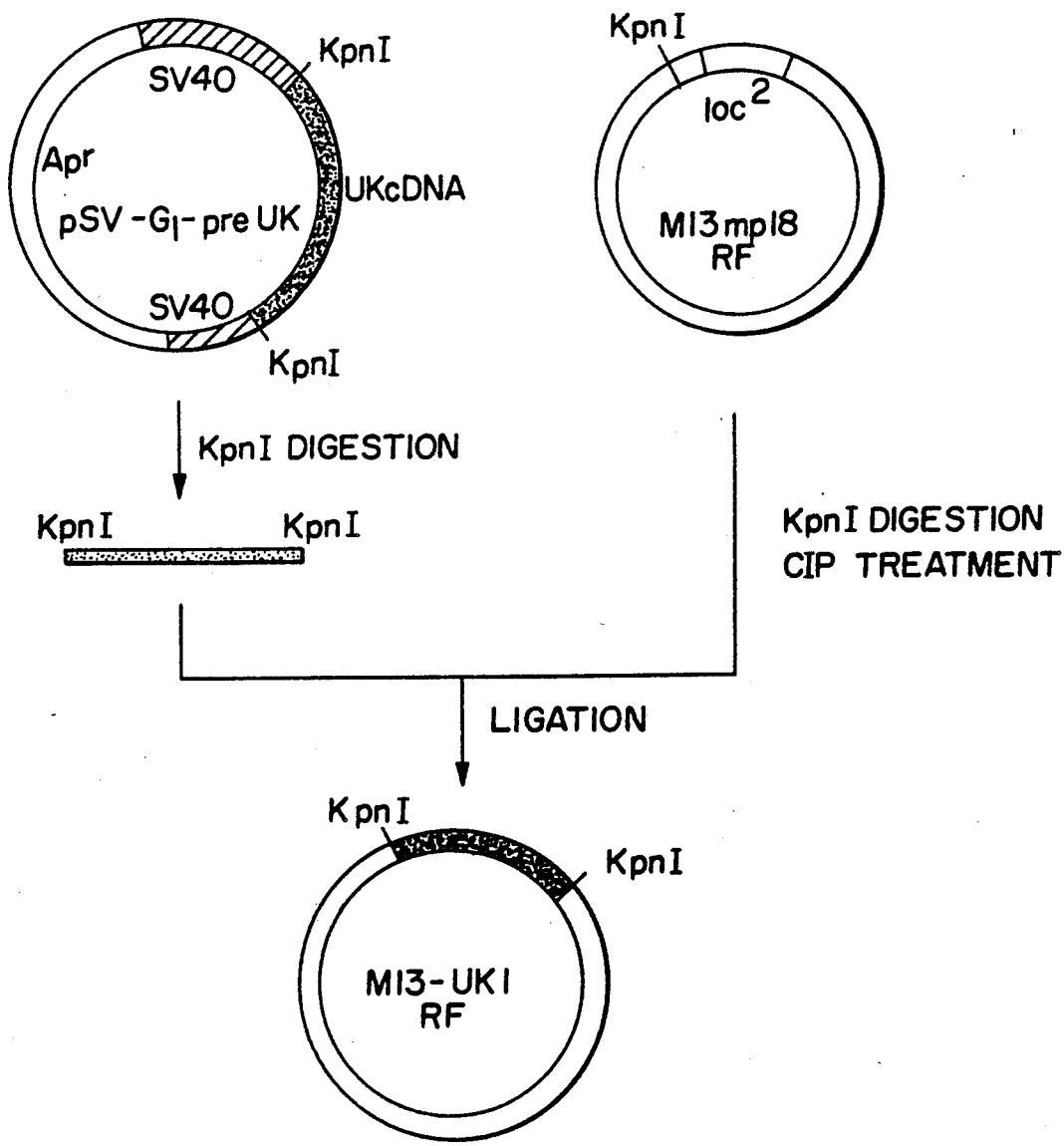
FIG. 4 shows the insertion of a preUK cDNA fragment into the M13mp18R plasmid.

For locating novel unique restriction enzyme sites on the human PUK gene by the technique of site-specific mutagenesis a KpnI fragment of the plasmid pSV-$G_1$-preUK was first introduced into the M13mp18RF plasmid (Takara Shuzo Co., Ltd.; Messing et al., Method in Enzymology, 101, 20–78) (FIG. 4).

More specifically, 10 μg of the psV-$G_1$-preUK plasmid was completely digested with 30 units of the restriction enzyme KonI at 37° C. This DNA digest was subjected to 1% (w/v) agarose gel electrophoresis and a 1.7 kb KonI fragment was recovered from the gel. (The techniques used are all as described by T. Maniatis et al. in "Molecular Cloning", Cold Spring Harbor Laboratory (1982).) Then, 1 μg of the M13mp18RF plasmid was completely digested with 3 units of KpnI and, 5'-end dephosphorylation was effected using calf intestinal alkaline phosphatase (CIP). This KpnI-digested M13 plasmid was mixed with the 1.7 kb KonI fragment prepared as above and, after addition of 30 units of T4 DNA ligase, the ligation reaction was carried out as described in the above-mentioned technique of Maniatis et al. After the reaction, the resulting DNA was used to transform the Escherichia coli strain JM105 (Amersham Inc.).

(C) DNA base substitution using the technique of site specific mutagenesis

Site specific mutagenesis was effected by the method of Zoller, M.J. et al., DNA, 3, 479 (1984) and of Wells, J.A. et al., Gene, 34, 315 (1985).

Figure 5:
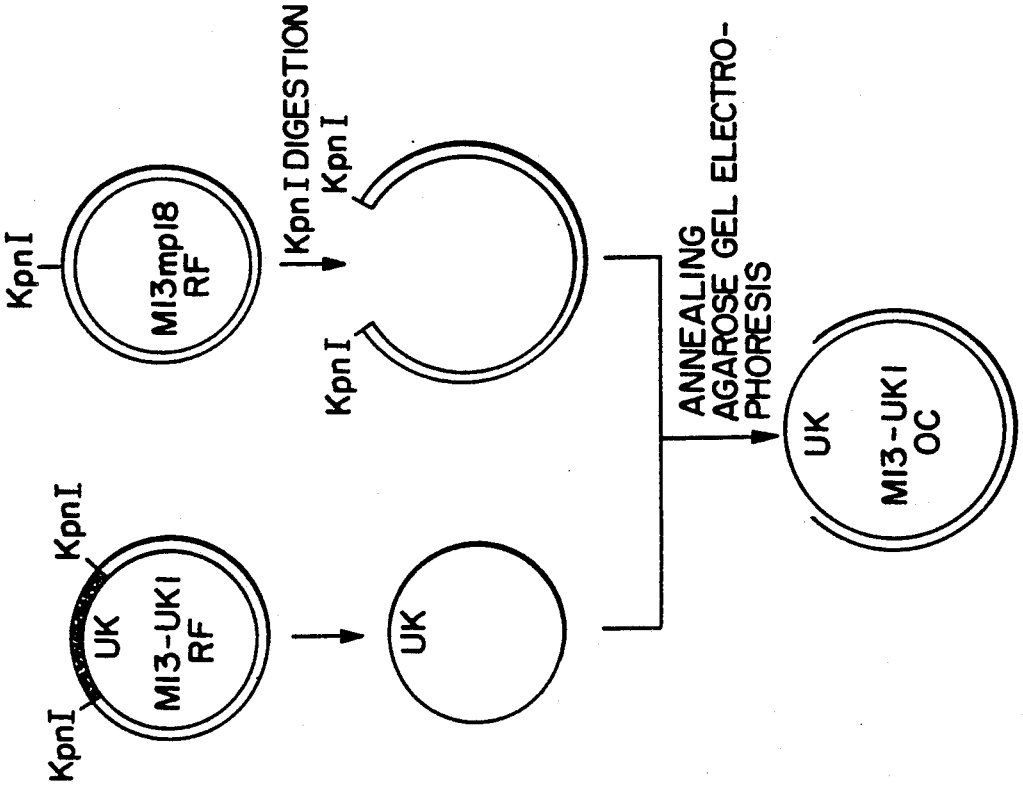
FIG. 5 shows the construction scheme or an open circular plasmas, M13-UK1-OC.

More specifically, a single-stranded DNA was prepared from the Escherichia coli JM105 transformant containing the M13-UK1RF plasmid (FIG. 4). This operation was conducted as described by Sanger, F. et al., J. Mol. Biol., 143, 161 (1980). Then 10 μg of this single-stranded M13-UK1 DNA (SS-M13-UK1) was mixed with 10 μg of the M13m18 fragment obtained by KpnI digestion. The mixture was heated to 100° C. for 2 minutes, then gradually cooled to 65° C. for annealing of SS-M13-UK1 with the negative strand of M13m18-KpnI, and quenched in ice. Thereafter, this DNA was applied to 0.8% (w/v) agarose gel, and the desired double-stranded open-circular-form DNA portion, DNA M13-UK1-OC (FIG. 5) was recovered.

Then, for base substitution, two oligonucleotides were synthesized. One was a mutagenesis primer for introduction of an SacI site (primer (i)) and the other was a mutagenesis primer for introduction of an NdeI site (primer (ii)). Each was 22mer 2-base-mismatch nucleotide are both shown in Table 2.

TABLE 2

Two synthetic oligonucleotide primers i) Mutagenesis primer for insertion at the SacI site

| | −1 | 1 | 2 | 3 | 4 | 5 | 6 | 7 | |
|---|---|---|---|---|---|---|---|---|---|
| Amino acid | Gly | Ser | Asn | Glu | Leu | His | Gln | Val | |
| Wild type | 5'- GGC | AGC | AAT | GAA | CTT | CAT | CAA | GTT | -3' |
| Mutagenesis primer i) | 3'- CCG | TCG | TTA | CT C | GA C | GTA G | GTT | C | -5' |

SacI site ii) Mutagenesis primer for insertion at the NdeI site

| | 46 | 47 | 48 | 49 | 50 | 51 | 52 | 53 | |
|---|---|---|---|---|---|---|---|---|---|
| Amino acid | Lys | Ser | Lys | Thr | Cys | Tyr | Glu | Gly | |
| Wild type | 5'- AAG | TCA | AAA | ACC | TGC | TAT | GAG | GGG | -3' |
| Mutagenesis primer ii) | 3'- TC | AGT | TTT | TGG | A GT | ATA | CTC | CC | -5' |

NdeI site

Figure 6:
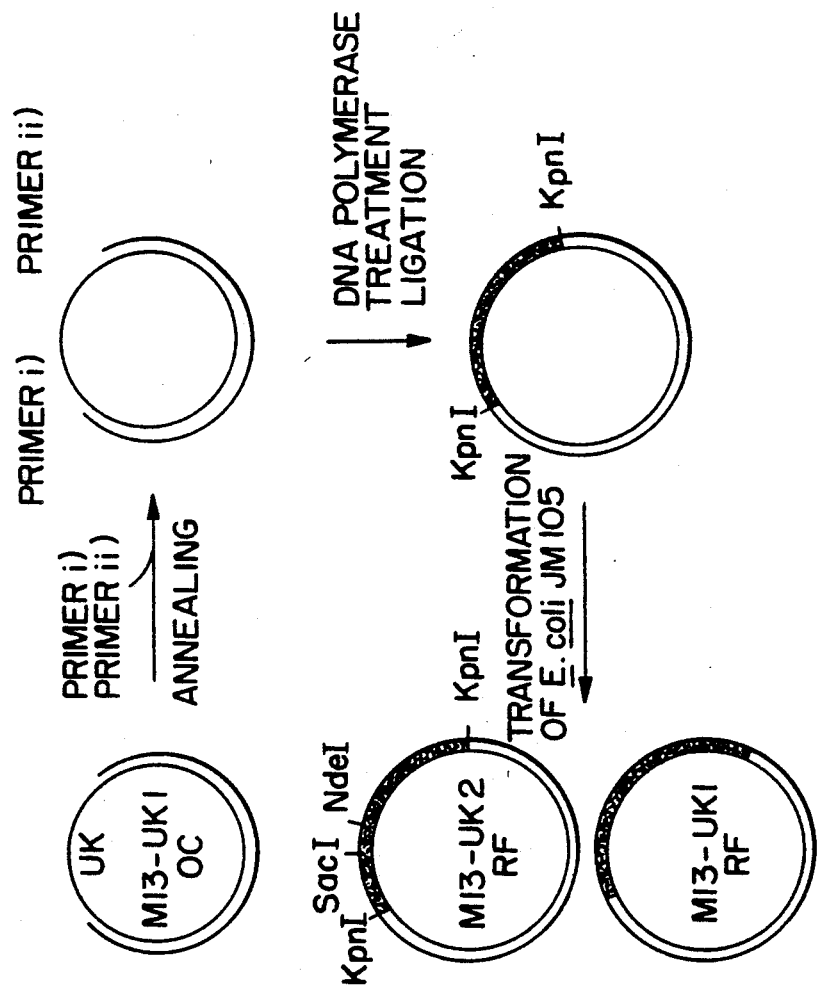
FIG. 6 shows a process for introducing a SacI site and an NdeI site into the human PUK gene.

The above two oligonucleotide primers were phosphorylated at the 5' end using T4 polynucleotide kinase. These two primers (100 pmol each) were then added, together with 1 pmol of the M13-UK1-OC DNA, to annealing buffer (20 mM Tris-HCl, 10 mM MgCl$_2$, 50 mM NaCl, 1 mM DTT, pH 7.5). The mixture was heated at 55° C. for 10 minutes and then allowed to stand at room temperature for 20 minutes for annealing of the plasmid with the two primers. Then, an equal volume of Pol I ligation buffer (20 mM Tris-HCl, 10 mM MgCl$_2$, 10 mM DTT, pH 7.5, 0.5 mM dNTPs, 1 mM γATP, 10 units T4 DNA ligase, 5 units E. coli DNA polymerase large fragment) was added, and the reaction was carried out at 15° C. for 8 hours. This reaction mixture was then used to transform the E. coli JM105 strain (FIG. 6). For selecting strains carrying the plasmid M13-UK2RF with the SacI and NdeI sites introduced in the human PUK gene from among a number of transformants, plaque hybridization was carried out using the mutagenesis primers as hybridization probes.

More specifically, 200 to 300 plaques per plate were transferred to a nitrocellulose filter. The nitrocellulose filter was used after immersion in a 100-fold dilution of an overnight E. coli JM105 culture fluid for 5 minutes, followed by air drying. The resulting filter was placed on H agar with the plaque surface up and was allowed to stand overnight at 37° C. The phage DNA was then immobilized by the method of T. Maniatis et al., Molecular Cloning, 1982. This filter was subjected to prehybridization and hybridization by the method of Zoller, M.J. et al., DNA, 479 (1984). The two mutagenesis primers labeled with (γ-$^{32}$P)ATP at the 5' end were used as the hybridization probes. After hybridization using each probe, washing was performed with 6×SSC. The washing temperature was raised stepwise to 25° C., 48° C., 56° C., and 64° C., whereby the wild type DNA was washed off at 56° C. or below while the mutant DNA remained hybridized. As a result of hybridization screening of about 1,000 plaques, seven clones remained which hybridized with both the probes even after washing at 64° C. These seven clones were plaque-purified by the method of Zoller, M.J. et al., DNA, 3, 479 (1984). Each plaque was diluted with TE and added in an H agar medium together with an E. coli JM105 culture fluid. For each clone, 10 plaques were subjected to dot hybridization. In this hybridization, too, the two mutagenesis primers were used as the probes. The DNA base sequence for each positive clone from the dot hybridization was determined by the dideoxy method of Sanger et al., Proc. Natl. Acad. Sci. USA, 74, 5463 (1977). As a result, five clones containing the SacI and NdeI sites were obtained. The plasmid of these clones was named M13-UK2RF (FIG. 6).

(D) Construction of an expression vector for expression of EGF-domain-deficient human PUK mutant The plasmid M13-UK2RF (5 μg) was digested with 20 units of KpnI. Separately, the NdeI site of the plasmid pSVG$_1$ was eliminated by filling in and, then, 1 μg of this plasmid was digested with 3 units of KpnI. Both the DNAs were mixed together and the ligation reaction was carried out using 10 units of T4 DNA ligase. This DNA solution was used to transform the Escherichia coli strain HB101 (Takara Shuzo). From among the resulting transformants (Ap$^r$), was obtained a clone, HB101/pSV-UK10, carrying the desired, SacI site- and NdeI site-containing plasmid pSV-UK10 (FIG. 1).

An expression vector for a human PUK mutant deficient in 36 amino acid residues for Asn-10 and Asp-45 was constructed using the plasmid pSV-UK10. Since digestion of pSV-UK10 with the restriction enzymes SacI and NdeI results in elimination from the human PUK gene of the condons for the 4th amino acid (leucine) from the N terminus to the 50th amino acid (cysteine) (Table 3A). oligonucleotides (Table 3B) were synthesized to give a DNA fragment coding for His-5 to Ser-9 plus Lys-46 to Cys-50 and having an SacI and an NdeI digestion terminus.

TABLE 3

SacI-NdeI digestion/cleavage region (A) of pSV-UK10 and synthetic oligonucleotide (B) for insertion at said site

A:

| -20 | | | | | | | | | | | | | | | | | |
|---|---|---|---|---|---|---|---|---|---|---|---|---|---|---|---|---|---|
| MET | ARG | ALA | LEU | LEU | LEU | ALA | ARG | CYS | VAL | LEU | VAL | SER | ASP | SER | LYS | GLY | |
| ATG | AGA | GCC | CTG | CTG | CTG | GCG | GGC | TGC | GTC | CTG | GTC | AGC | GAC | TCC | AAA | GGC | |

| 1 | 2 | 3 | 4 |
|---|---|---|---|
| SER | ASN | GLU | LEU |
| AGC | AAT | GAG | CT |
| TCG | TTA | C | |

| | | | | | | | | | 51 | | | | | | | | | 60 |
|---|---|---|---|---|---|---|---|---|---|---|---|---|---|---|---|---|---|---|
| ALA | SER | THR | ASP | MET | GLY | ARG | PRO | CYS | TYR | GLU | GLY | ASN | HIS | PHE | TYR | ARG | GLY |
| GCC | AGC | ACT | GAC | ATG | GGC | CGG | CCC | TGC | TAT | GAG | GGG | AAT | CAC | TTT | TAC | CGA | GGA |
| | | | | | | | | | A | CTC | CCC | TTA | GTG | AAA | ATG | GCT | CCT |

| 61 | | | | | | | | | | | | | | | | | | |
|---|---|---|---|---|---|---|---|---|---|---|---|---|---|---|---|---|---|---|
| LYS | ALA | THR | TYR | HIS | ALA | HIS | MET | ARG | SER | ASP | ALA | LEU | LEU | TRP | ASN | SER | ALA | VAL |
| AAG | GCC | CAC | AGA | TCT | GAT | ATG | GCT | CTT | CAG | CTG | GGC | CTG | TGG | AAC | TCT | GCC | GTC | |
| | | | 7 | 8 | 9 | | | 46 | 47 | 48 | 49 | 50 | | | | | | |
| | | | VAL | PRO | SER | | | LYS | SER | LYS | THR | CYS | | | | | | |

| 81 | | | | | | | | | | | | | |
|---|---|---|---|---|---|---|---|---|---|---|---|---|---|
| GLN | THR | TYR | HIS | ALA | ARG | SER | ASP | ALA | LEU | GLN | LEU | GLY | LEU |
| CAT | GCC | CAC | AGA | TCT | GCT | CTT | CAG | CTG | GGC | CTG | GGG | AAA | CAT |
| 3 | 5 | 6 | | | | | | | | | | | |
| (GLU | HIS | GLN | | | | | | | | | | | LYS |
| LEU) | | | | | | | | | | | | HIS | — |

ASN -CAG CAA AGG

B:

5'- C   CAT GTT CCA TCG AGC TCG AGT TTT AAA ACC TGC AT -3'
3'- TC GAG GTA CAA GGT AGC TCG AGC TCA AAA TTT TGG ACG AT -5'

Figure 7:
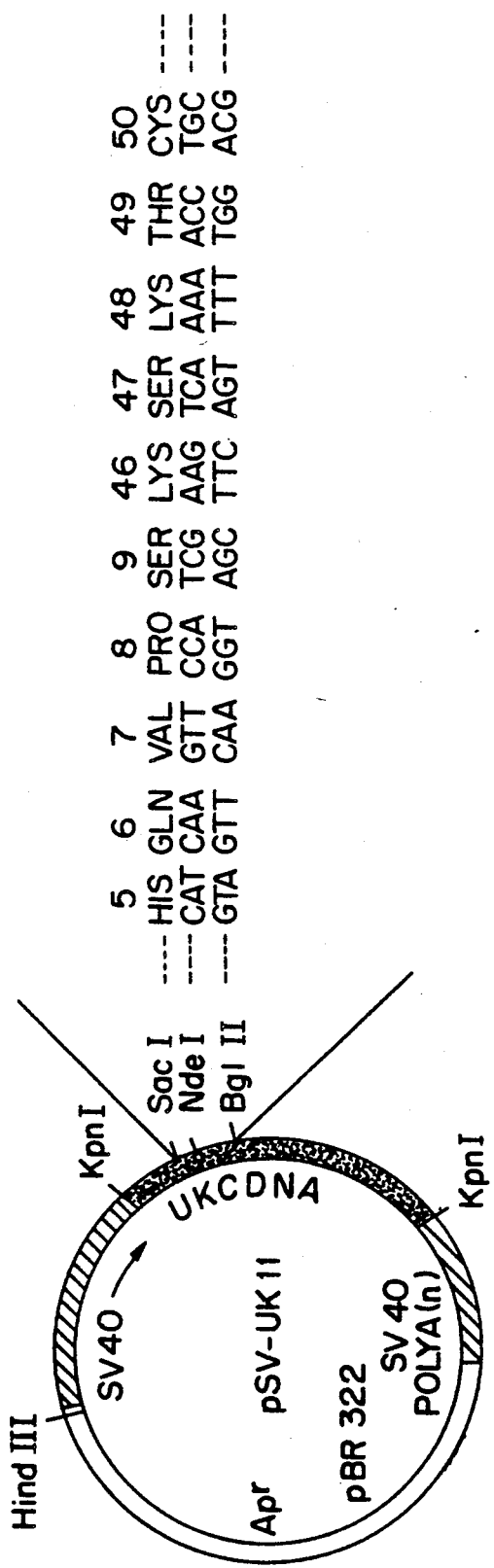
FIG. 7 shows the structure of the mutant PUK expression vector, pSV-UK11.

The 31 mer and 37 mer oligonucleotides synthesized (each 50 pmol) were mixed together, and the mixture was heated to 70° C. and then allowed to stand at room temperature for 20 minutes for annealing. The resulting DNA and 1 μg of the SacI-NdeI digest fragment of the plasmic pSV-UK10 were mixed together and ligated using 30 units of T4 DNA ligase. As a result, a vector, pSV-UK11, allowing expression in animal cells of a human PUK mutant deficient in the 10th amino acid (asparagine) residue from the N terminus of human PUK to the 45th amino acid (aspartic acid) residue was constructed (FIG. 7).

In the same manner, various synthetic genes were inserted in the SacI-NdeI site and expression vectors for human PUK mutants characterized by various forms of variation (deletion, and substitution of amino acid residue) within the region from Leu-4 to Cys-50 of human PUK were constructed.

(E) Construction of derivatives within the kringle domain of human PUK

Figure 8:
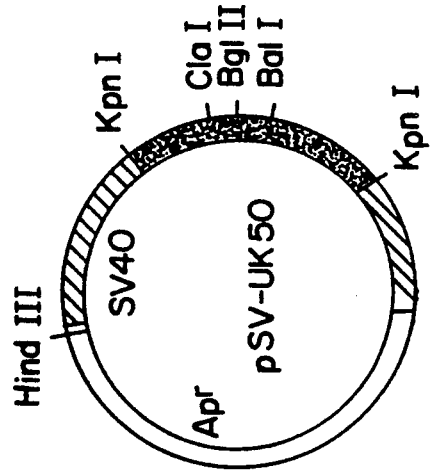
FIG. 8 shows the restriction enzyme map of the plasmid, pSV-UK50.

Using the same technique of site-specific mutagenesis as mentioned above, ATA (Ile-44) was converted to ATC and, as a result, an expression vector, pSV-UK50, having a ClaI restriction enzyme site within the DNA base region coding for Ile-44 to Asp-45 was constructed (FIG. 8).

Digestion of pSV-UK50 with ClaI and BglII, ClaI and BalI, or BglII and BalI followed by insertion, at the resulting site, of a variety of synthetic oligonucleotides in the same manner as above led to construction of expression vectors for human PUK mutants modified within the kringle domain.

(F) Production of human PUK mutants in animal cells

The expression vectors for human PUK mutants were introduced onto the chromosome of Chinese hamster ovary cells (CHO-K$_1$, ATCC CCL61) using pSV-G$_1$-Neo as a dominant selective marker. The construction of pSV-G$_1$-Neo, cotransfection of CHO-K$_1$ cells was the same together with the human PUK mutant expression vector and cloning were performed as described in Japanese Patent Application (OPI) No. 60-180591.

The clone, CHO-UK11, as transformed with the plasmid pSV-UK11 (deficient in condons for Asn-10 to Asp-45) was cultured and the culture supernatant assayed for plasminogen activator activity. Thus, when first subjected to a fibrin-agar plate assay, the supernatant was found active. This activity was neutralized by anti-human urokinase antibody. Further screening gave a strain, CHO-UK11-7, which appears capable of higher productivity of the human PUK mutant. Using the culture supernatant of this clone, the properties of the mutant human PUK protein produced were investigated.

(G) Purification of the human PUK mutant produced in the cell line CHO-UK11-7

CHO-UK11-7 cells suspended in 5 ml of Ham's F-12 medium containing 5% (w/v) of fetal calf serum were placed in a 25-cm$^3$ culture flask (Corning #25100) ($5 \times 10^{-5}$ cells per flask). After 3 days of incubation, when the culture was confluent, the cells were washed with several portions of Ham's F-12 medium (without addition of fetal calf serum). Thereafter, Ham's F-12 medium containing aprotinin (10 KIU/ml) and 0.1% (w/v) human serum albumin was used as a maintenance medium, with the culture medium exchanged at 2- to 3-day intervals. The mutant human PUK was purified from 1 liter of this serum-free culture supernatant. More specifically the culture supernatant was adjusted to pH 5.5 by adding 1N HCl and, then, a suspension of CM-Sephadex C-50 (Pharmacia) (in an amount corresponding to 1.5 g on the dry basis) in 0.16M sodium phosphate (pH 5.5) was added. The mixture was stirred at 4° C. for 2 hours. The gel was recovered on a glass filter, washed with 0.16M sodium phosphate (pH 5.5). and packed into a column (2.5×10 cm). Elution was carried out with 0.16M sodium phosphate (pH 8.5). An active eluate fraction showing fibrinolytic activity on a fibrin-agar plate (J. Cell Biol., 94, 631 (1982)) was poured into a column (1.5×10 cm) packed with Sepharose 4B (gel volume: 9 ml) with anti-urokinase polyclonal antibody (freed from protease activity by passage through DEAE Affi-Gel Blue. p-Aminobenzamidine-Sepharose or Lysine-Sepharose) immobilized thereon. After washing the antibody column with 0.5 M NaCl-0.1M sodium phosphate (pH 7.0). elution was carried out with 0.2M glycine-HCl-0.5M NaCl (pH 2.5). An active fraction showing fibrinolytic activity on a fibrin-agar plate was recovered, adjusted to pH 7.0 by dropwise addition of 1 M aqueous Tris, and subjected to the subsequent analysis of its properties:

(1) Molecular weight

The molecular weight of the CHO-UK11-7 cell-derived human PUK mutant was determined by the SDS-polyacrylamide gel electrophoretic method described in Nature, 227, 680 (1970). Under reducing as well as non-reducing conditions, the molecular weight was found to be about 45 kilodaltons. The above result shows that the CHO-UK11-7 cell-derived human PUK mutant has a single-chain structure with a molecular weight of about 45 kilodaltons.

(2) Enzyme susceptibility

The urokinase activity of the CHO-UK11-7 cell-derived human PUK mutant was determined by measuring the amidase activity against the synthetic substrate S-2444 (Kabi) for a urokinase activity assay. Human urine-derived urokinase was used as a control. More specifically, a 1 μg/ml solution of the CHO-UK11-7 cell-derived human PUK mutant or human urine-derived urokinase in 0.05M Tris-HCl, 0.038M NaCl 0.2% (w/v) BSA (pH 8.8) was prepared and treated with a plasmin in known concentrations at 37° C. for 1 hour, and the urokinase activity thus expressed was determined using the synthetic substrate S-2444 (J. Biol. Chem., 260, 12377 (1985)). The CHO-UK11-7 cell-derived human PUK mutant itself did not show urokinase activity. However, plasmin treatment resulted in expression of urokinase activity (Table 4).

TABLE 4

| Urokinase activity after plasmin treatment (IU/ml) | | | | | |
|---|---|---|---|---|---|
| | No plasmin treatment | Plasmin concentration (mCU/ml) | | | |
| | | 0.375 | 1.5 | 6 | 12 |
| Human urine urokinase | 151 | 153 | 149 | 152 | 150 |
| CHO-UK11-7 cell-derived mutant human PUK | 0.6 | 91 | 122 | 140 | 138 |

This enzyme activity was destroyed by anti-urokinase polyclonal antibody. This revealed that the CHO-UK11-7 cell-derived human PUK mutant is an enzyme which is in an inactive form but is capable of expressing urokinase activity upon plasmin treatment.

EXAMPLE 2

(A) Construction of EGF domain-deficient mutant human PUK genes

Figure 9:
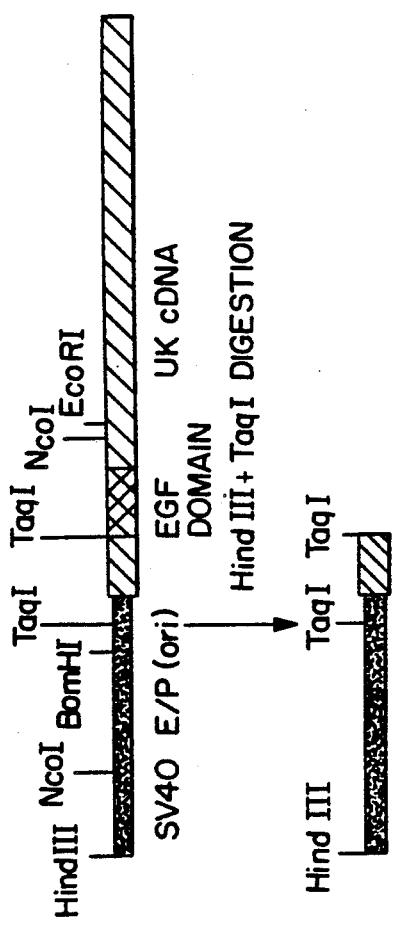
FIG. 9 shows the process for preparing plasmids pUH7 to 9.
Figure 9:
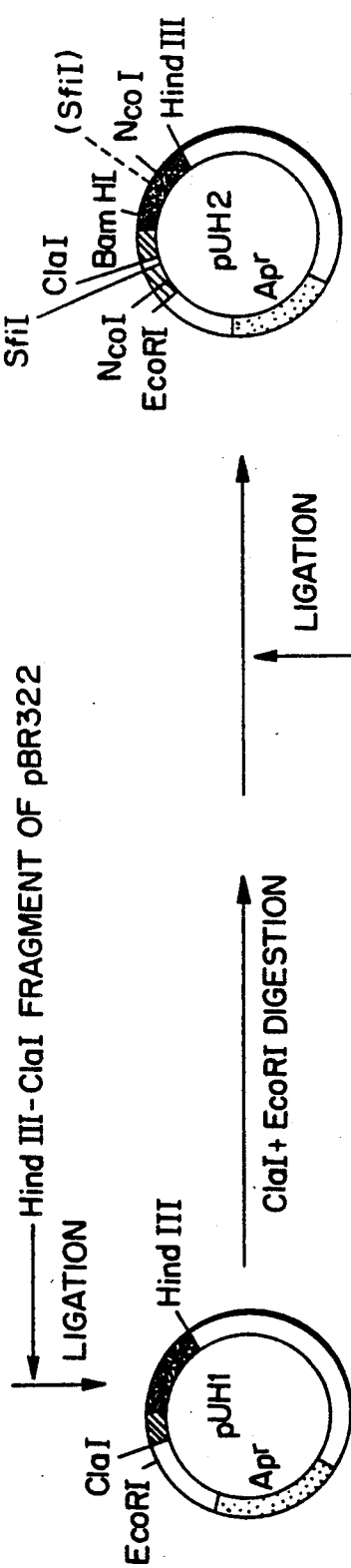
Figure 9:
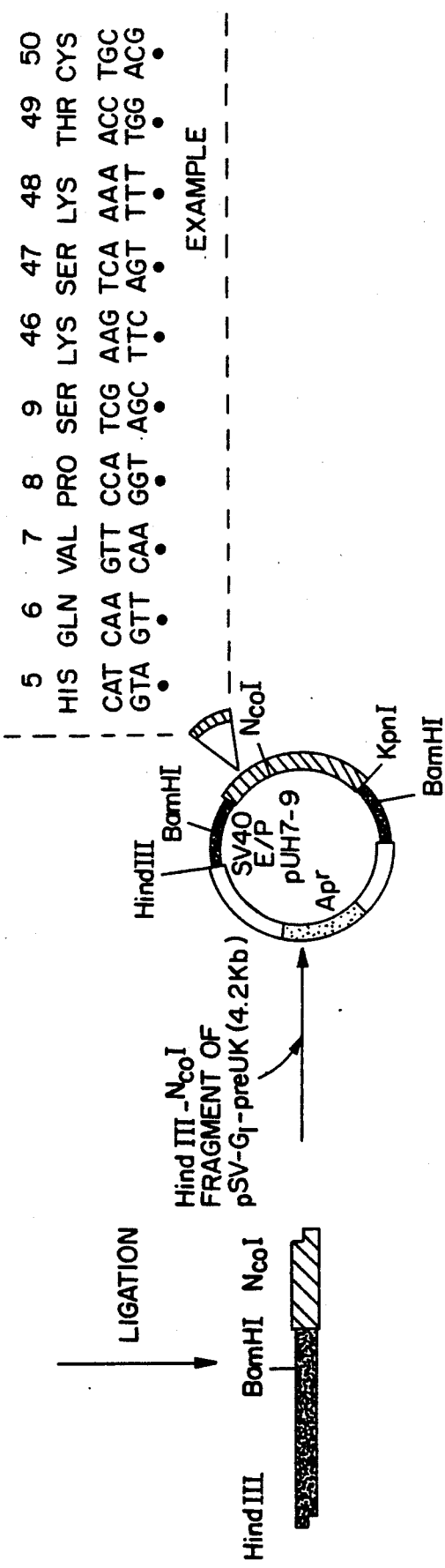

Three expression vectors for human PUK deficient in the EGF domain regions of Asn-10 to Cys-42, Asn-10 to Asp-45, and Asn-10 to Thr-49, respectively, were constructed. The method of deleting each EGF domain-encoding region from the human PUK gene and the construction schemes for the respective expression vectors for use in animal cells are outlined in FIG. 9.

Thereafter, the EGF domain encoding regions from the human PUK gene were eliminated by utilizing the NcoI and TaqI sites proximal to said regions. More specifically, the expression vector for human PUK pSV-G1-preUK was digested with HindIII and TaqI, and a partial human PUK gene fragment containing the coding region for the N terminus to the 10th amino acid residue (Asn) was isolated and inserted into the plasmid pBR322, whereby the plasmid pUH1 was constructed. Then, a synthetic gene coding for the region from Asn-54 to Met-67 of human PUK and having ClaI and EcoRI sites a the termini thereof was prepared and inserted into the plasmid pUH1 to give the plasmid pUH2. This synthetic gene was also provided with an SfiI site.

The BamHI-EcoRI fragment containing only the SfiI site on the synthetic gene was inserted into the BLUESCRIBE plasmid (Vector Cloning). Thus was constructed the plasmid pUH3. Three plasmids (pUH4 to pUH6) having the partial human PUK (N terminus to Met-67) genes deprived of the respective EGF domain regions were constructed by inserting three synthetic genes coding for Cys-50 to Gly-53, Lys-46 to Gly-53, and Glu-43 to Gly-53, respectively and having a ClaI and an SfiI site at the respective ends into pUH3 at the SfiI-ClaI site. Then, for inserting these EGF domain-deficient regions into an expression vector, the BamHI-NcoI fragment of each of pUH4 to pUH6 and the HindIII-BamHI fragment of pSV-preUK were joined together. The resulting fragment was inserted into pSV-G1-preUK in the HindIII-NcoI region. In this manner, three expression vectors, pUH7 to pUH9, for the corresponding EGF domain-deficient human PUK mutants were constructed. The construction of these expression vectors is described below in further detail. In this example, unless otherwise specified, each DNA digestion with a restriction enzyme or enzymes was carried out overnight at 37° C. The digestion of DNA prepared by the alkaline denaturation (mini-prep) method was performed using 5 units of restriction enzyme per microgram of DNA. The buffer compositions for restriction enzymes were as recommended by the enzyme suppliers. The ligation reaction was carried out at 16° C. for 1 to 2 hours using DNA ligation kits (Takara Shuzo) and the following reaction mixture composition:

| | |
|---|---|
| DNA fragment | 5.0 μl (500 ng) |
| Vector DNA | 2.5 μl (250 ng) |
| Buffer A[1] | 60.0 μl |
| Buffer B[2] | 7.5 μl |
| | 75.0 μl |

[1] Takara ligation kit reaction buffer A
[2] Takara ligation kit enzyme solution B The DNA base sequence determination was made by the dideoxy sequencing method using the plasmid obtained by the alkaline denaturation method.

(1) Synthesis of oligonucleotides

Nine oligonucleotides having oligonucleotides sequences shown in Table 5 below were synthesized using an automatic DNA synthesizer.

TABLE 5

Sequence of oligonucleotides synthesized by automated DNA synthesizer

| Length (-mer) | Sequence (5' → 3') | Used |
|---|---|---|
| 11 | CCCTCATAGC A | Synthetic gene |
| 16 | CGTGCTATGA GGGGAA | Synthetic gene |
| 18 | GAACTTCATC AAGTTCCA | Sequencing primer |
| 23 | CCCTCATAGC AGGTTTTTGA CTT | Synthetic gene |
| 28 | CGAAGTCAAA AACCTGCTAT GAGGGGAA | Synthetic gene |
| 32 | CCCTCATAGC AGGTTTTTGA CTTATCGATT TC | Synthetic gene |
| 37 | CGGAAATCGA TAAGTCAAAA ACCTGCTATG AGGGGAA | Synthetic gene |
| 54 | CGATAGGCCG GAATGGCCAC TTTTACCGCC GAAAGGCTAG CACTGACACC ATGG | Synthetic gene |
| 56 | AATTCCATGG TGTCAGTGCT AGCCTTTCCG CGGTAAAAGT GGCCATTCCG GCCTAT | Synthetic gene |

One of them was used as a sequencing primer and the others were all used as synthetic genes. The oligonucleotides synthesized were treated for deprotection and then separated and purified by denaturing gel electrophoresis. A portion of each purified oligonucleotide was labeled with $^{32}P$ at the 5' end for purity checking. Each oligonucleotide was observed as a single band irrespective of size.

(2) Annealing

Four synthetic genes shown in Table 6 were prepared by annealing each complementary pair of synthetic oligonucleotides in sequence to each other.

TABLE 6

| Gene | Annealed* DNA length |
|---|---|
| 54                                            67 <br> ASN GLY HIS PHE TYR ARG GLY LYS ALA SER THR ASP THR MET <br> 5'-CGATAGGCCGG AAT GGC CAC TTT TAC CGC GGA AAG GCT AGC ACT GAC ACC ATG G <br>     TATCCGGCC TTA CCG GTG AAA ATG GCG CCT TTC CGA TCG TGA CTG TGG TAC GTTA <br> ClaI      SfiI                                                 NheI      NcoI     EcoRI <br> (TaqI) | 56-mer <br> 54-mer |

TABLE 6-continued

| Gene | Annealed* DNA length |
|---|---|
| 43                                      53<br>GLU ILE ASP LYS SER LYS THR CYS TYR GLU GLY<br>5'-CG GAA ATC GAT AAG TCA AAA ACC TGC TAT GAG GCG AA<br>     CTT TAG CTA TTC AGT TTT TGG ACG ATA CTC CC<br>            ClaI | 37-mer<br>32-mer |
| 46                          53<br>LYS SER LYS THR CYS TYR GLU GLY<br>5'-CG AAG TCA AAA ACC TGC TAT GAG GGG AA<br>     TTC AGT TTT TGG ACG ATA CTC CC | 28-mer<br>23-mer |
| 50           53<br>CYS TYR GLU GLY<br>5'-CG TGC TAT GAG GGG AA<br>     ACG ATA CTC CC | 16-mer<br>11-mer |

This annealing reaction was effected by heating at 75° C. for 10 minutes followed by gradual cooling to 20° C. over 3 hours. The reaction mixture composition was used as follows:

| Oligonucleotide a | 10 μl (100 pmol) |
| Oligonucleotide b | 10 μl (100 pmol) |
| 10 × buffer A* | 3 μl |
| Redistilled water | 7 μl |
| | 30 μl |

*10 × buffer A:
100 mM Tris-HCl, pH 7.6
5 mM MgCl₂

An equimolar mixture of the 56mer and 54mer oligonucleotides each labeled with $^{32}P$ at the 5' end was gradually cooled from 75° C. to 20° C. and the degree of annealing was examined by electrophoresis. Free single-stranded DNAs were almost absent and the DNAs were mostly in the double-stranded form. Therefore, other oligonucleotides were subjected to annealing under the same conditions and the partial genes thus constructed were inserted into various plasmids.

(3) Construction of the plasmids pUH1 to pUH3

Since a number of TacI sites are present on the plasmid pSV-G1-preUK. it is difficult to cause cleavage only at the TagI site proximal to the EGF domain through the use of one restriction enzyme treatment alone. Therefore, a DNA fragment containing this TagI site was excised. More specifically, pSV-G1-preUK was digested with the restriction enzymes HindIII and BglII and the resulting DNAs examined by agarose gel electrophoresis. A 1.1 kb DNA fragment containing the EGF domain-encoding region was recovered from the corresponding gel portion excised from the gel. Then, this fragment was partially digested with TagI and the digest subjected to polyacrylamide gel electrophoresis. After confirmation of the presence of the desired 760 bp band, this DNA fragment was recovered.

Separately, the plasmid pBR322 was digested with HindIII and ClaI, whereby a 4.3 kb DNA fragment was obtained. This DNA was ligated with the 760 bp HindIII-TagI DNA fragment prepared previously. This ligation caused conversion of the TacI site originally occurring at the 3' end of the 760 bp fragment to a ClaI site. The reaction mixture was used to transform the E. coli strain HB101. The DNAs prepared from 24 transformant strains were each digested with ClaI and NcoI. The desired plasmid pUH1 (FIG. 9) was expected to be cleaved with either ClaI or NcoI only at one site. Electrophoresis revealed 6 clones to be the desired plasmid.

Then pUH1 was digested with EcoRI and ClaI, followed by agarose gel electrophoresis. An about 5.0 kb DNA fragment was recovered from the gel, and this DNA was ligated with the annealing product from the 56mer and the 54mer synthetic oligonucleotides prepared in steps (1) and (2) mentioned above. The reaction mixture was used to transform E. coli HB101. DNAs prepared from 20 transformant strains were digested with NcoI and EcoRI-HindIII. The desired plasmid pUH2 would give an about 700 bp DNA upon digestion with NcoI and about an 810 bp DNA fragment upon EcoRI-HindIII digestion. Electrophoresis revealed 4 clones to be the desired plasmid.

Since pUH2 contains two SfiI sites in close vicinity to each other, the BamHI-EcoRI fragment containing the synthetic gene-derived SfiI site was transferred to another vector. Thus, pUH2 was first digested with BamHI and EcoRI. The digest was subjected to polyacrylamide gel electrophoresis. A 330 bp DNA fragment was recovered from the corresponding gel portion by electroelution.

Separately the plasmid BLUESCRIBE (Vectorcloning Systems) was digested with BamHI and EcoRI. and the about 3.1 kb DNA fragment obtained was ligated with the 330 bp BamHI-EcoRI fragment prepared previously, and this reaction mixture was used to transform the E. coli strain JM105. Twelve strains were selected from among the transformants obtained and the DNA prepared from each of the twelve strains was digested with SfiI and ClaI. If the DNA is the desired plasmid pUH3. it is cleaved only at one site with each of SfiI and ClaI. As a result of electrophoresis, eight clones were found to carry the desired plasmid.

(4) Construction of the plasmids pUH4 to pUH9

An attempt was made to construct the plasmids pUH4 to pUH6 having partial genes for human PUK deprived of the EGF domain by inserting the three synthetic genes into the plasmid pUH3 in the ClaI-SfiI, and an about 3.1 kb DNA fragment was recovered by agarose gel electrophoresis followed by electroelution. This fragment was ligated with each of the three synthetic genes. These reaction mixtures were used to transform the E. coli strain JMI05. For each synthetic gene, 10 strains were selected from among the transformants obtained, and the DNA prepared from each strain was digested with BamHI and EcoRI. If the DNA is the desired plasmic pUH4, pUH5, or pUH6, it gives, upon restriction enzyme digestion, a 360 bp fragment (in the case of pUH4), a 2,350 bp fragment (in the case of pUH5) or a 340 bp fragment (in the case of pUH6). As a result of checking by polyacrylamide gel electrophoresis, 2 clones of pUH4, 2 clones of pUH5 and 3 clones of pUH6 were obtained.

Using these plasmids, the DNA base sequences in the EGF domain region were determined. As a result, it was found that the regions intended for deletion had been deleted without causing any change in the remaining amino acid sequence.

Then, the SV40 early gene promoter region-EGF domain-deficient human PUK mutant-encoding partial gene portion was excised from each of the plasmids pUH4 to pUH6 and incorporated in the human PUK expression vector pSV-G1-preUK for use in animal cells. More specifically, pUH4 to pUH6 were cleaved with NcoI and then subjected to CIP treatment for dephosphorylation at the 5' end. These DNAs were digested with BamHI, the digests subjected to polyacrylamide gel electrophoresis, and a 360 bp DNA fragment (from pUH4), a 350 bp DNA fragment (from pUH5) and a 340 bp DNA fragment (from pUH6) were recovered by electroelution from the corresponding gel segments excised from the polyacrylamide gel. These DNAs were each ligated with a 400 bp BamHI-HindIII fragment of the plasmid pSV-G1-preUK as separately prepared. After the ligation reaction, DNAs were recovered by precipitation with ethanol.

Separately, pSV-G1-preUK was digested with HindIII and NcoI and the digest was subjected to electrophoresis. An about 4.2 kb DNA fragment segment was excised from the gel and the DNA recovered by electroelution. This 4.2 kb HindIII-NcoI DNA fragment was religated with the above-mentioned three ligation samples. Each reaction mixture was used to transform the E. coli strain HB101. For each reaction mixture 16 strains were selected from among the transformants obtained. The DNA extracted from each strain was digested with HindIII and with HINdIII and BglII. If the DNA is the plasmid pUH7, pUH8 or pUH9, HindIII digestion gives an about 4.9 kb DNA fragment and HindIII-BlgII digestion gives an about 1.0 kb fragment. As a result of electrophoresis, 3 clones of pUH7, 3 clones of pUH8 and 5 clones of pUH9 were obtained. For each plasmid, one clone was selected and used for large quantity preparation of the plasmid. The structure of the plasmids thus obtained were analyzed in further detail (Table 7).

for EGF domain-deficient human PUK mutants, pUH7 to pUH9, were constructed.

Based on the results of measurement of the above-mentioned restriction enzyme digest fragments, it is believed that no substantial deletion is found in other parts than the EGF domain. Sequencing of the neighborhood of the deleted portion failed to reveal any change in base sequence. In view of the above, it is believed that no deletion or mutation occurred at places other than the region in question.

(5) Production of EGF domain-deficient human PUK mutants in COS7 cells

The three expression vectors pUH7 to pUH9 were each introduced, in an amount of 20 μg, into COS7 cells ($3 \times 10^6$ cells), and the activity of each expression product and the productivity was investigated (Table 8).

TABLE 8

| | Production of human PUK mutants by COS7 cells | | | |
|---|---|---|---|---|
| | Serum-free medium | | 10% Fetal calf serum-containing medium | |
| Cells Cultured | Fibrin plate method (IU/ml) | RPHA method (units/ml) | Fibrin plate method (IU/ml) | RPHA method (units/ml) |
| pUH7 | 180 | 200 | 140 | 150 |
| pUH8 | 180 | 150 | 120 | 150 |
| pUH9 | 160 | 150 | 140 | 150 |
| pSV-G1-preUK | 120 | 120 | 80 | 100 |

(Human urinary urokinase, 1,150 IU/ampoule, was used as a reference standard.)

More specifically, after DNA introduction, the COS cells were cultured in D-MEM (Nissui Seiyaku) containing 10% (w/v) FCS (GIBCO) or in a serum-free medium containing 10 KIU/ml of aprotinin (SIGMA). In each case, the culture was sampled after 72 hours of incubation and assayed for plasminogen activator activity by the fibrin-agar plate method and for antigen quantity by the RPHA assay method. For each clone, and irrespective of the presence or absence of serum, the production was about 200 IU/ml and there was no substantial difference between the biological activity value and the activity value calculated on the basis of the antigen quantity. The above findings demonstrate that deletion of the EGF domain does not influence the expression of plasminogen activator activity.

(6) Introduction of expression vectors for EGF domain-deficient human PUK mutants into CHO cells

TABLE 7

| Restriction enzyme treatment of human PUK mutant expression vectors | | | | | | | | |
|---|---|---|---|---|---|---|---|---|
| | | | | Fragment Size (Kb) | | | | |
| Plasmid | ClaI | HindIII | BamHI | | KpnI | HindIII + BglII | BGlII + KpnI | |
| pUH7 | 4.9 | 4.9 | 3.1 | 1.3 | 3.5 | 3.9 | 3.5 | 1.0 |
| | | | 0.3 | | 1.4 | 1.0 | 0.4 | |
| pUH8 | 4.9 | 4.9 | 3.1 | 1.3 | 3.5 | 3.9 | 3.5 | 1.0 |
| | | | 0.3 | | 1.4 | 1.0 | 0.4 | |
| pUH9 | 4.9 | 4.9 | 3.1 | 1.3 | 3.5 | 3.9 | 3.5 | 1.0 |
| | 0.8 | | 0.3 | | 1.4 | 1.0 | 0.4 | |
| pSVG1-UK | 5.0 | 5.0 | 3.1 | 1.4 | 3.5 | 3.9 | 3.5 | 1.0 |
| | | | 0.3 | | 1.5 | 1.1 | 0.5 | | pUH7: Deficient in the region Asn(10)-Cys(42)
pUH8: Deficient in the region Asn(10)-Asp(45)
pUH9: Deficient in the region Asn(10)-Thr(49)

The sizes of fragments obtained by digestion with a variety of restriction enzymes perfectly agreed with the anticipated values. In this way, three expression vectors The three human PUK mutant expression vectors were introduced into CHO K1 cells (ATCC CCL61).

More specifically, the plasmids pUH7 to pUH9 were introduced into CHO K1 cells together with pSV-G1-

Neo by the DNA-calcium phosphate precipitate method. The cells were cultured in a medium containing G418. The resulting resistant colonies were transferred to 96-well plates by the cloning cylinder method. The efficiency of plasmid introduction was $1.2 \times 10^{-5}$ colonies/μg/dish for pUH7, $3.2 \times 10^{-4}$ colonies/μg/dish for pUH8, and $3.9 \times 10^{-4}$ colonies/μg/dish for pUH9. There were no great differences among the three plasmids.

For the G418-resistant colonies obtained by transfection, the 96-well plate culture supernatants were assayed for plasminogen activator (PA) activity using the fibrin-agar plate method. For each plasmid, about 130 clones were examined for PA production. Ten clones in the case of pUH7, 8 clones in the case of pUH8 and 16 clones in the case of pUH9 showed a production of not less than 25 IU/ml. In particular, in the case of pUH9, one clone showed a production as high as 100 IU/ml or more. However, the status of growth and multiplication differed from clone to clone on the 96-well plates and therefore exact comparison with respect to productivity could not be made. Therefore, these clones were cultivated on a large scale and compared with respect to PA production.

More specifically, each clone was cultured on Ham's F12 medium containing 10% (w/v) FCS and when the culture became confluent, the PA production was determined. As a result, transfection with pUH7 gave a clonal strain, U7-2, showing a maximum productivity of about 13 IU/ml/day, while transfection with pUH8 gave a clonal strain, U8-65, showing a productivity of 30 IU/ml/day at most. For each of these clones, the PA activity of the culture supernatant was completely neutralized by anti-urokinase polyclonal antibody.

The three strains U7-2, U8-65 and U9-25 that were highly productive for mutant human PUK, were cultured for a period of time and changes in productivity followed. The strain U9-25 did not show any substantial changes in productivity for about one month. As a result of rescreening of these highly productive strains the clonal strain U7-2-23, showing a high productivity of 222 IU/ml/day was obtained from strain U7-2; the clonal strain U8-65-34, showing a productivity of 52 IU/ml/day was obtained from strain U8-65; and the clonal strain U9-25-6, showing a productivity of 200 IU/ml/day was obtained from strain U9-25. These strains obtained by rescreening all showed no substantial decrease in productivity even after passage of about one month.

(7) Culturing method

For the passage of C-68-53 cells and human PUK mutant-producing CHO cells, Ham's F12 medium containing 10% (w/v) FCS was used. For a property analysis and activity assay, the following culturing was carried out. First, the cells were grown on Ham's F12 medium containing 10% (w/v) FCS until confluency. The cells were then washed well two or three times with Ham's F12 medium (serum-free) so that serum components could be removed as completely as possible. Thereafter, the cells were maintained in Ham's F12 medium (serum-free) or the same medium containing 10% (w/v) FCS for 2 to 3 days. In case of protease inhibitor addition, aprotinin was added to a concentration of 10 KIU/ml. After completion of cultivation, the culture supernatant was centrifuged (3,000 rpm, 5 minutes, Hitachi model 05P-2113 table centrifuge) and stored in a frozen state at $-40°$ C. until use.

The experiments on the effects of medium and additives in serum-free cultivation of human PUK mutant-producing CHO cell strains were carried out as follows: Cells were suspended in Ham's F12 medium, F12-MW (a mixture of Ham's F12 medium and modified Waymouth medium), or RITC medium, each of these contained 5% (v/v) FCS. The suspended cells were then transferred to 75 cm³ flasks ($2 \times 10^6$ cells per flask). After 2 days of incubation, the cells were washed three times with the corresponding serum-free medium and 25 ml of a serum-free, additive-containing culture medium was poured into each flask. Thereafter, the medium was replaced with a fresh portion at 2-day intervals.

(8) Property analysis of human PUK mutants

Cells were multiplied until confluent. Then, maintenance culturing was conducted using medium containing 1% (w/v) FCS, serum-free medium containing aprotinin, and the culture supernatants from these cultures were subjected to fibrin autography. For all the human PUK mutant-producing strains, the culture supernatant gave a band showing PA activity in the vicinity of molecular weight 45.000. While serum-free culture supernatants gave only a band in the neighborhood of a molecular weight of 45,000, the supernatants obtained from cultures in the presence of 1% (v/v) FCS gave a further band indicating a lower molecular weight substance and one more band indicative of higher molecular weight complex although the amounts of these substances were fairly small.

Western blotting was then conducted with the same culture supernatants as mentioned above. Each culture supernatant was subjected to SDS-polyacrylamide gel electrophoresis, followed by Western blotting analysis using anti-urokinase polyclonal antibody. The culture supernatants obtained by the use of the strains U7-2, U8-65 and U9-25 gave a main band reactive with the antibody in the neighborhood of a molecular weight of 45,000. Reduction treatment did not cause a shifting of the band to the lower molecular weight side. On the other hand, with C-68-53, i.e., a natural human PUK-producing cell line, the culture supernatant gave a single band corresponding to a molecular weight of about 50,000 under reducing conditions as well as under non-reducing conditions. Urine-derived high-molecular urokinase gave a single band corresponding to a molecular weight of 50,000 under non-reducing conditions and, under reducing conditions, it gave a single band corresponding to a molecular weight of 33,000.

The above results indicate that the three kinds of human PUK mutant produced in CHO cells were all in the single chain form with a molecular weight of 45,000. The difference of about 5,000 in molecular weight from natural human PUK agreed with the molecular weight value calculated form the number (about 40) of amino acid residues in the deleted EGF domain region.

The culture supernatants obtained from serum-free culture and culture with 10% (v/v) FCS were assayed for PA activity using the fibrin-agar plate method and for antigen quantity using the RPHA method. Each clone exhibited no substantial difference between the biological activity value and the activity value calculated from the antigen quantity, irrespective of the presence or absence of serum (Table 9).

TABLE 9

Production of human PUK mutants by CHO cells

| Cells Cultured | Serum-free medium | | 10% Fetal calf serum-containing medium | |
|---|---|---|---|---|
| | Fibrin plate method (IU/ml) | RPHA method (units/ml) | Fibrin plate method (IU/ml) | RPHA method (units/ml) |
| U7-2 | 90 | 75 | 130 | 90 |
| U8-65 | 8 | 8 | 7 | 8 |
| U9-25 | 150 | 100 | 150 | 150 |
| C-68-53 | 55 | 75 | 45 | 60 |

The above findings demonstrate that the deletion of the EGF domain does not affect the expression of PA activity.

Thereafter, whether the three human PUK mutants produced in CHO cells are proenzymes and whether they are activated by plasmin in the same manner as natural human PUK were investigated (Table 10).

TABLE 10

Conversion of human PUK mutants produced in CHO cells to the active form by plasmin treatment

| Cells cultured | PA activity (units/ml) | | Fibrin-agar plate method |
|---|---|---|---|
| | Plasmin (−) | After plasmin treatment (+) | |
| U7-2 | <3.2 | 85 | 90 |
| U8-65 | <3.2 | 16 | 16 |
| U9-25 | <3.2 | 120 | 150 |
| C-68-53 | <3.2 | 67 | 55 |

For each clone, urokinase activity could not be detected without plasmin treatment. For each clone, plasmin treatment carried out under the same conditions as in the activation of natural human PUK increased the urokinase activity to a level almost equal to the activity value obtained by the fibrin-agar plate method.

It was thus revealed that these human PUK mutants, all produced as proenzymes, can be converted satisfactorily to the active form by plasmin treatment under the same conditions as used in the case of natural human PUK.

(9) Method of purification

Chelating Sepharose 6B (100 ml) was packed into a column, 2.5×20 cm in size, and washed with 500 ml of 0.5M EDTA-NaOH, pH 8.0, and 500 ml of water in that order. Then, 500 ml of 0.035M $ZnCl_2$ (pH 4.2) was poured into the column for binding of the $Zn^{2+}$ ion to the gel. Unbound $Zn^{2+}$ ions were washed away with water and the column was equilibrated with a buffer 0.02M Tris-HCl, 1M NaCl aprotinin (10 KIU/ml), 0.01% (w/v) Tween 80, pH 7.5 (buffer A). The supernatant of a serum-free culture of CHO cells producing a human PUK mutant was then supplied to the column at a flow rate of 200 ml/hr (40 ml/hr/$cm^2$) using a peristapump. The column thus charged with the sample was washed with buffer A and the human PUK mutant was eluted on a linear imidazole concentration gradient made up with 120 ml of buffer A and 120 ml of buffer A containing 0.05M imidazole. A similar experiment was carried out using Chelating sepharose Fast Flow Column (100 ml, 2.5×20 cm). In this case, however, the rate of supply of the human PUK mutant-producing CHO cell culture supernatant was 400 ml/hr (80 ml/hr/$cm^2$). The active eluate fraction from the Chelating Sepharose 6B column was poured into an anti-UK IgG-Sepharose 4B column (8 ml, 1.5×4 cm). This column was washed with 0.5M NaCl-0.1M sodium phosphate-0.01% (w/v) Tween 80, pH 7.0, and the human PUK mutant was eluted with 0.5M NaCl-0.2M glycine-HCl-0.01% (w/v) Tween 80, pH 2.5. The active eluate fraction was adjusted to pH 7.0 by addition of solid-form Tris and poured into a p-aminobenzamidine-Sepharose 6B column (20 ml, 1.555×10 cm). This column was washed with 0.4M NaCl-0.1M sodium phosphate-0.01% (w/v) Tween 80, pH 7.0, and the substance adsorbed was eluted with 0.4M NaCl-0.1M sodium acetate-0.01% (w/v) Tween 80, pH 4.0. By this procedure, the human PUK mutant was recovered into an unadsorbed fraction.

In the above manner, a human PUK mutant as produced in a serum-free medium with a specific activity of 27 IU/$A_{280}$ could be purified to a specific activity of 6.9×$10^4$ IU/$A_{280}$; the degree of purification was 2,411 times and the recovery was 71%.

(10) Amino acid sequences of human prourokinase mutants

The amino acid sequence in the amino terminal region of each of the human PUK mutants produced by the strains U7-2 (a strain of CHO K1 transfected with the plasmid pUH7), U8-65-34 (a strain of CHO K1 transfected with the plasmid pUH8) and U9-25 (a strain of CHO K1 transfected with the plasmid pUH9) was determined by using a gaseous-phase protein sequencer and compared with the amino acid sequence of human kidney cell-derived PUK (Kasai, S. et al., *J. Biol. Chem.*, 260, 12382 (1985)) (Table 11).

TABLE 11

```
        1                            11                           21                        30
(I):    Ser-Asn-Glu-Leu-His-Gln-Val-Pro-Ser-Asn-Cys-Asp-Cys-Leu-Asn-Gly-Gly-Thr-Cys-Val-Ser-Asn-Lys-Tyr-Phe-Ser-Asn-Ile-His-Trp- 1                  9
(II):   Ser-Asn-Glu-Leu-His-Gln-Val-Pro-Ser- 1                  9
(III):  Ser-Asn-Glu-Leu-His-Gln-Val-Pro-Ser- 1                  9
(IV):   Ser-Asn-Glu-Leu-His-Gln-Val-Pro-Ser- 31                            41                          51                          60
(I):    Cys-Asn-Cys-Pro-Lys-Lys-Phe-Gly-Gly-Gln-His-Cys-Glu-Ile-Asp-Lys-Ser-Lys-Thr-Cys-Tyr-Glu-Gly-Asn-Gly-His-Phe-Tyr-Arg-Gly-...

10                                          60
(II):                                          -Glu-Ile-Asp-Lys-Ser-Lys- * - ° -Tyr-Glu-Gly-...

10                          20
(III):                                         -Lys-Ser-Lys-Thr- * -Tyr-Glu-Gly-Asn-Gly-His-...
```

TABLE 11-continued

|  | 10 | 20 |
|---|---|---|
| (IV): | -*-Tyr-Glu-Gly-Asn-Gly-His-Phe-Tyr-Arg-Gly-... | |

*The gaseous-phase protein sequencer failed to identify the asterisked amino acid residues.
(I): Human kidney cell-derived PUK
(II): U7-2 cell strain-derived PUK mutant
(III): U8-65-34 cell strain-derived PUK mutant
(IV): U-9-25 cell strain-derived PUK mutant As a result, it was revealed that the human PUK mutants derived from the strains U7-2, U8-65-34 and U9-25 were deficient in Asn-10-Cys-42, Asn-10-Asp-45 and Asn-10-Thr-49 of human kidney cell-derived PUK, respectively. These human PUK mutants had a molecular weight of about 45,000, which was smaller by about 5,000 than the molecular weight of human kidney cell-derived PUK. This molecular weight difference agreed with the number of the amino acid residues (33 to 40) deficient in the human PUK mutants. Based on the above results, it is estimated that there was no deletion, mutation or the like in other regions than the Asn-10-Thur-49 region.

(11) Half-life in blood

Comparison between the human PUK mutants obtained in this example and human kidney cell-derived PUK (*J. Biol. Chem.*, 260, 12377 (1985)) was made with respect to half-life of rat blood. More specifically, rats were anesthetized with ether and the carotid artery was cannulated. After administration of the $^{125}$I-labeled form of the human PUK mutant or human kidney cell-derived PUK into the caudal vein at a dose of $10^6$ cpm, rat blood samples were taken at timed intervals via the cannule inserted into the carotid artery and measured for radioactivity contained therein using a gamma counter.

The half-lives in blood of the human PUK mutants obtained in this example were determined in the same manner as in Example 1. The results are shown in Table 12, below.

TABLE 12

| | Half-life in Blood (min.) |
|---|---|
| Human kidney cell-derived PUK | 1.63 ± 0.05 |
| Mutant PUK deficient in the Asn-10-Cys-42 region | 8.24 ± 1.46 |
| Mutant PUK deficient in the Asn-10-Asp-45 region | 6.25 ± 0.32 |
| Mutant PUK deficient in the Asn-10-Thr-49 region | 7.13 ± 0.33 |

The above results show that the EGF domain region-deficient human PUK mutants have longer half-lives in blood compared to human kidney cell-derived PUK. Similar results were also obtained in rabbits.

These results demonstrate that the EGF domain region in the PUK molecule is deeply involved in the kinetics of PUK in the body. Furthermore, the above results demonstrate the substitution of one or more amino acid residues occurring in the EGF domain region with one or more different amino acid residues can result in human PUK mutants deficient in EGF domain function but having a prolonged half-life in blood.

EXAMPLES 3 TO 5

Figure 10:
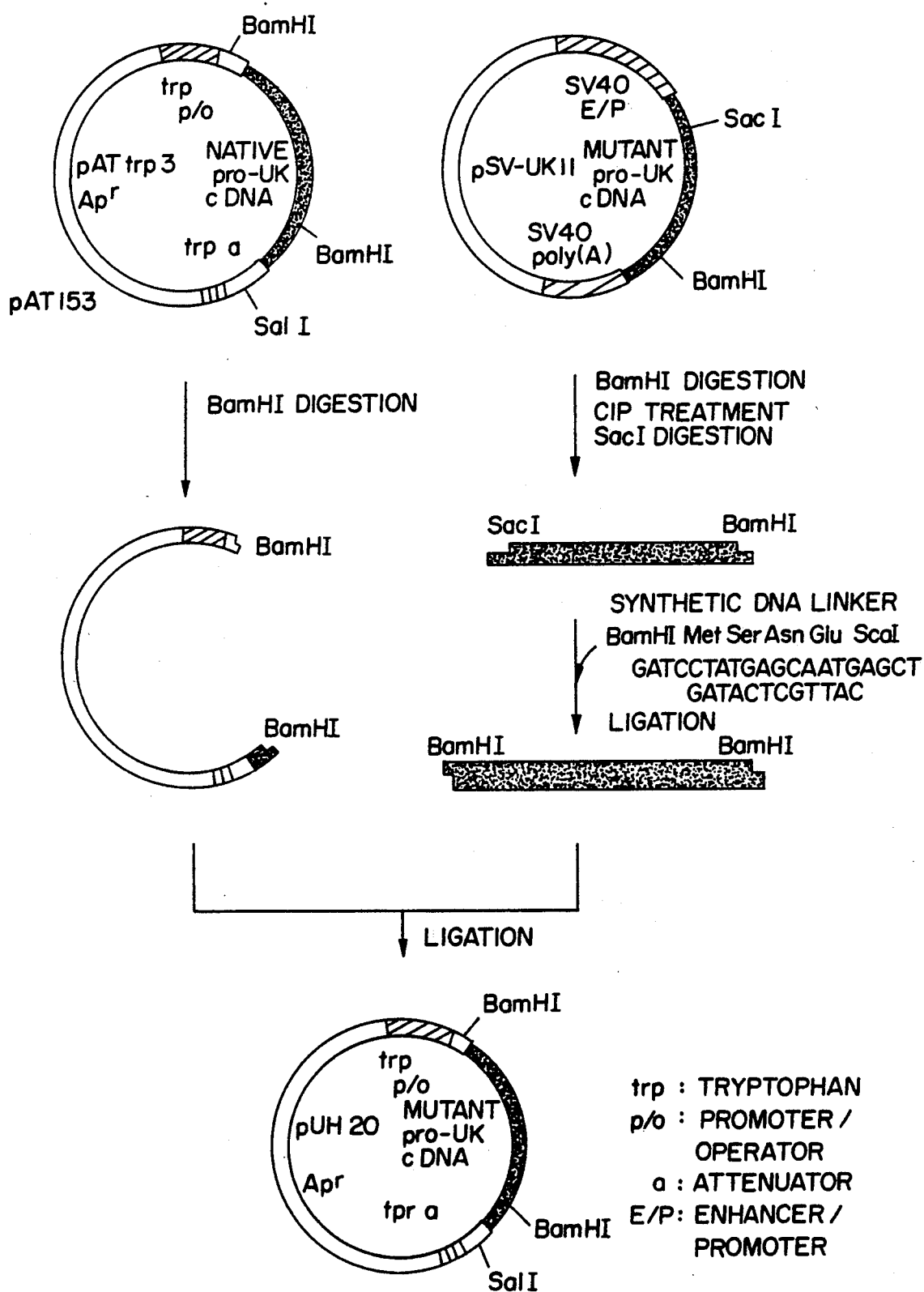
FIG. 10 shows an expression vector for use in *Escherichia coli.*
Figure 11:
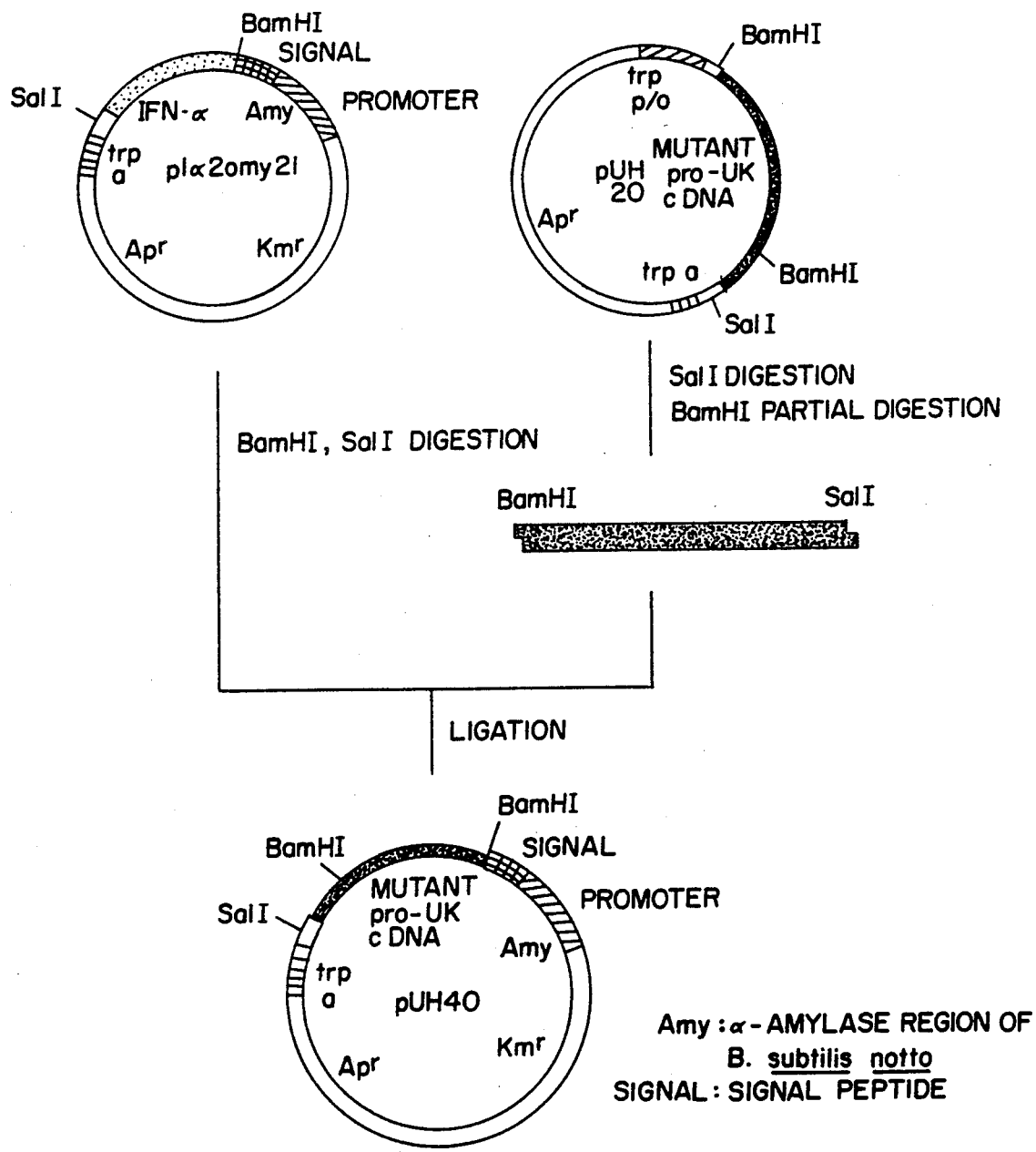
FIG. 11 shows an expression vector for use in *Bacillus subtilis.*
Figure 12:
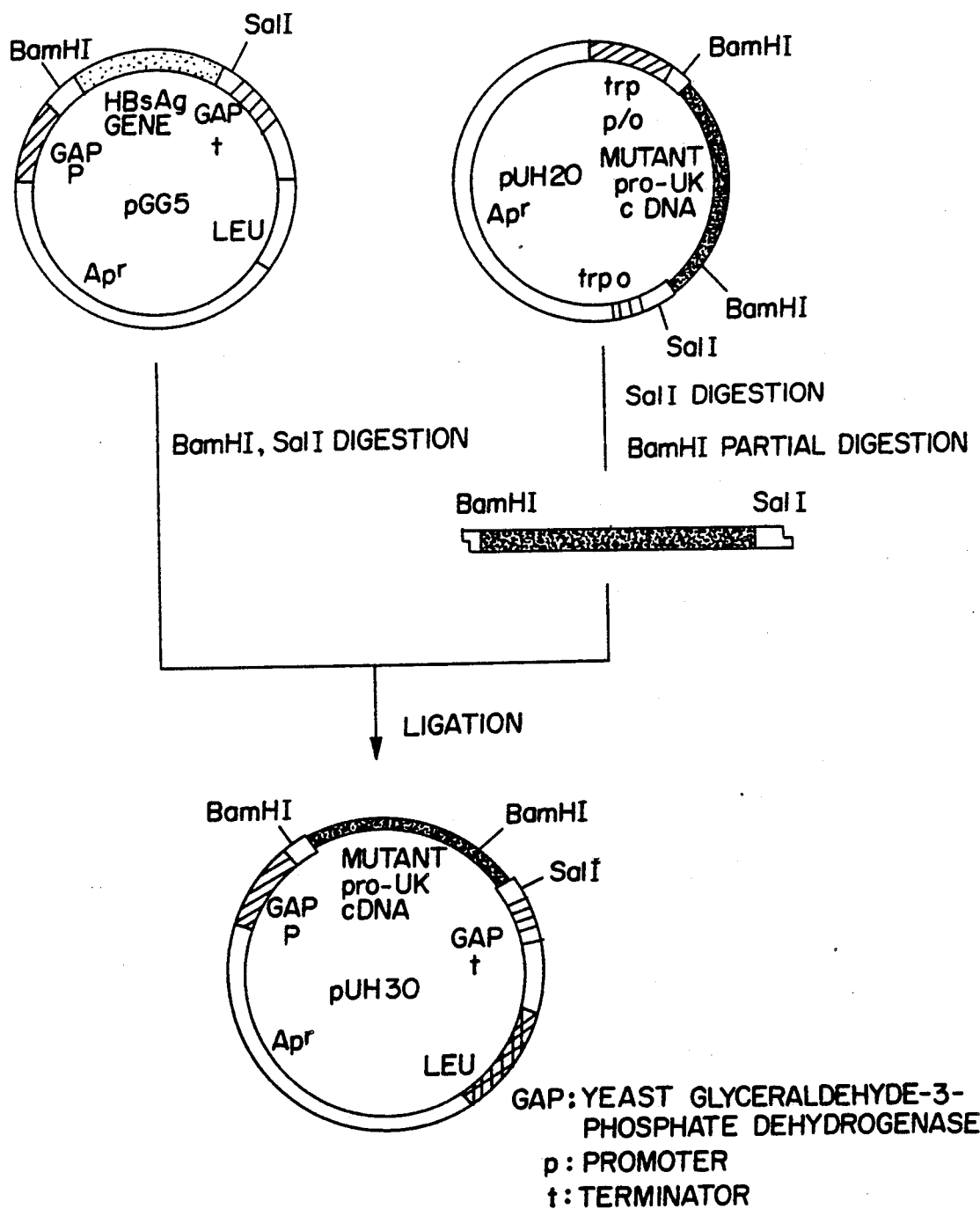
FIG. 12 shows an expression vector for use in *Saccharomyces cerevisiae.*

Expression vectors for use in *Escherichia coli, Bacillus subtilis* and yeasts, respectively for the expression of a human PUK mutant deficient in Asn(10)-Asp(45) were constructed as shown in FIG. 10 (construction of an expression vector for the expression Asn-10-Asp-45-deficient human PUK mutant in *Escherichia coli*), FIG. 11 (construction of an expression vector for the secretory expression of said human PUK mutant in *Bacillus subtilis*) and FIG. 12 (construction of an expression vector for the expression of said human PUK mutant in yeasts).

The activation of the plasmin was carried out by heating at 37° C. for 30 minutes at a plasmin concentration of 0.4 CU/ml. To 100 μl of a plasmin-treated or untreated sample, was added 5 μl of aprotinin (2×10$^4$ KIU/ml) for inactivation of the plasmin used for activation. Then, 695 μl of buffer A (0.05 M Tris-HCl, 0.038M NaCl, 0.2% (w/v) BSA, pH 8.8) and 100 μl of an aqueous solution of S-2444 (1.5 mg/ml) were added and changes in absorbance at 405 nm measured. By comparison with the absorbance values measured for known concentrations of urine-derived urokinase (Reference Standard GCC, 1,150 IU/ampoule), the urokinase activity of each sample was determined.

As described above, one aspect of the present invention demonstrates that a region (amino acid sequence) determining the half-life in blood (mainly the take-up by hepatocytes) should be present within the region composed of 33 amino acid residues from Asn-10 to Cys-42.

From the structural viewpoint, this region can be divided into three portions, namely Asn-10 to Cys-19, Val-20 to Asn-32, and Cys-33 to Cys-42. In view of the results of the secondary structure analysis of the Asn-10-Cys-42 region by the method of Chou and Fasman and the report on the binding of the epidermal growth factor (EGF), which is homologous to said region, to its receptor (Blomquist, M.C. et al., *Proc. Natl. Acad. Sci. USA*, 81. 7363 (1984)), among others, it is considered that the region concerned in the take-up by hepatocytes should be present within the Val-20-Cys-42 portion. The fact that Cys-33-Cys-42 portion alone is a highly hydrophilic amino acid region among the Asn-10-Cys-42 region and the report describing that the region (Cys-33 to Cys-42) in the amino acid sequence of epidermal growth factor, which is highly homologous to said Cys-33-Cys-42 portion, is associated with the affinity for (binding to) the epidermal growth factor receptor (Nestor, J.J. et al., *Biochem. Biophys. Res. Commun.*, 129, 226 (1985)), among others, lead to a presumption that the Cys-33-Cys-42 portion of human prourokinase is involved in the take-up by hepatocytes.

Therefore, human PUK mutants in which all or part of the Val-20-Cys-42 region of human PUK is absent or replaced by one or more different amino acid residues, DNA sequences coding for such human PUK mutants, and DNA sequences coding for human PUK mutants in which the entire or part of the Cys-33-Cys-42 region of human PUK is absent or replaced with one or more amino acid residues are also suitable embodiments of the present invention.

EXAMPLE 6

(1) Construction of pTT03

Figure 13:
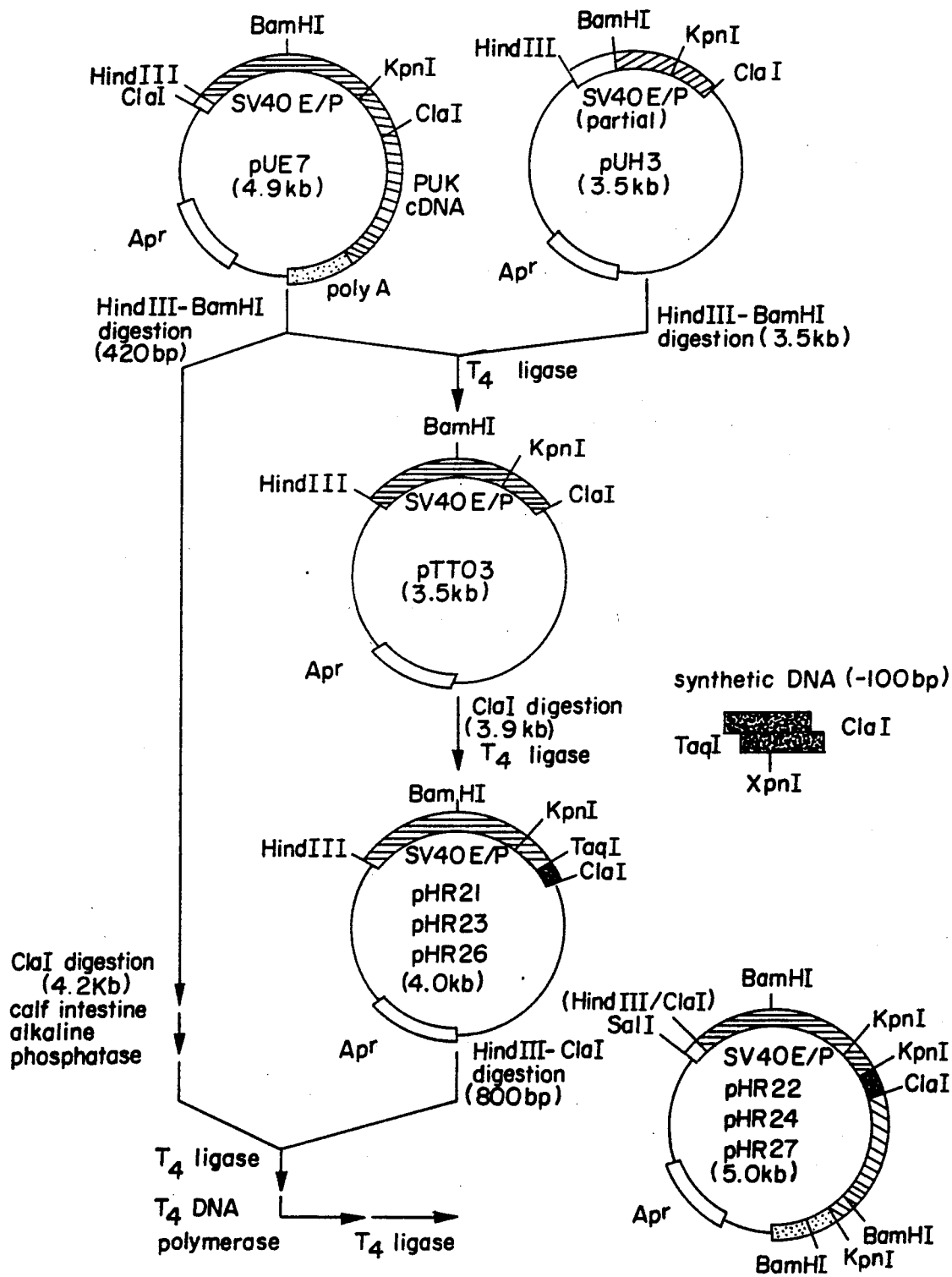
FIG. 13 shows a process for preparing plasmids pHR22, pHR24, and pHR27.

A plasmid pTT03, containing the SV40 enhancer-promoter region, the PUK signal sequence and a gene coding for Ser-1 to Ser-9 of PUK was constructed. For obtaining 5 regions of the SV40 enhancer-promoter with a BamHI recognition site, pUH7 was digested with HindIII and BamHI and a 420 bp fragment was isolated and purified by agarose gel electrophoresis. Separately, pUH3 was digested also with HindIII and BamHI and a linearized 3.5 kb DNA fragment was isolated and purified by agarose gel electrophoresis. This fragment was ligated to the above-mentioned 420 bp fragment with DNA ligase. A plasmid giving a 3.5 kb fragment and a 420 bp fragment upon digestion with HindIII and BamHI was named pTT03. Twelve transformants strains were examined and found all to be transformants harboring pTT03 (FIG. 13).

(2) Synthesis of oligonucleotides

Six single-stranded DNAs (DNA-1, DNA-2, DNA-3, DNA-4, DNA-5 and DNA-6) were prepared using an automatic DNa synthesizer (Applied Biosystems model 381A). Their base sequences are shown below.

For substituting Ser-4 for Tyr-24 (for carbohydrate addition on Asn-22):

```
DNA-1  5'- C G  AAC TGT GAC TGT CTA AAT
DNA-2  3'-      TTG ACA CTG ACA GAT TTA

Asn Cys Asp Cys Leu Asn

KpnI
       GGA GGTACC TGT GTC TCC AAC
       CCT CCA TGG ACA CAG AGG TTG

Gly Gly Thr Cys Val Ser Asn

SspI
       AAG TCC TTC TCC AATATT CAC
       TTC AGG AAG AGG TTA TAA GTG

Lys Ser Phe Ser Asn Ile His

TGG TGC AAC TGC CCA AAG AAA
       ACC ACG TTG ACG GGT TTC TTT

Trp Cys Asn Cys Pro Lys Lys

TTC GGA GGG CAG CAC TGT GAA
       AAG CCT CCC GTC GTG ACA CTT

Phe Gly Gly Gln His Cys Glu

AT    -3'
           TAGC  -5'

Ile
```

For substituting Asn-24 for Tyr-24 (for carbohydrate addition on Asn-24):

```
DNA-3  5'- C G  AAC TGT GAC TGT CTA AAT
DNA-4  3'-      TTG ACA CTG ACA GAT TTA

Asn Cys Asp Cys Leu Asn

KpnI
       GGA GGTACC TGT GTC TCC AAC
       CCT CCA TGG ACA CAG AGG TTG

Gly Gly Thr Cys Val Ser Asn
```

```
                     SspI
       AAG AAC TTC TCC AATATT CAC
       TTC TTG AAG AGG TTA TAA GTG

Lys Asn Phe Ser Asn Ile His

TGG TGC AAC TGC CCA AAG AAA
       ACC ACG TTG ACG GGT TTC TTT

Trp Cys Asn Cys Pro Lys Lys

TTC GGA GGG CAG CAC TGT GAA
       AAG CCT CCC GTC GTG ACA CTT

Phe Gly Gly Gln His Cys Glu

AT    -3'
           TAGC  -5'

Ile
```

For substituting Ser-29 for His-29 (for carbohydrate addition on Asn-27):

```
DNA-5  5'- C G  AAC TGT GAC TGT CTA AAT
DNA-6  3'-      TTG ACA CTG ACA GAT TTA

Asn Cys Asp Cys Leu Asn

KpnI
       GGA GGTACC TGT GTG TCC AAC
       CCT CCA TGG ACA CAC AGG TTG

Gly Gly Thr Cys Val Ser Asn

SspI
       AAG TAC TTC TCC AATATT TCC
       TTC ATG AAG AGG TTA TAA AGG

Lys Tyr Phe Ser Asn Ile Ser

TGG TGC AAC TGC CCA AAG AAA
       ACC ACG TTG ACG GGT TTC TTT

Trp Cys Asn Cys Pro Lys Lys

TTC GGA GGG CAG CAC TGT GAA
       AAG CCT CCC GTC GTG ACA CTT

Phe Gly Gly Gln His Cys Glu

AT    -3'
           TAGC  -5'

Ile
```

The first pair, DNA-1 and DNA-2, contains a DNA sequence coding for a PUK (Asn(10) to Ile(44)) but differing from PUK in that the thyrosine residue in position 24 has been replaced with a serine residue; the second pair DNA-3 and DNA-4, contains a DNA sequence coding for a PUK (Asn(10) to Ile(44)) but differing from PUK in that the thyrosine residue in position 24 has been replaced with an asparagine residue; and the third pair, DNA-5 and DNA-6, contains a DNA sequence coding for a PUK (Asn(10) to Ile(44)) but differing from PUK in that the histidine residue in position 29 has been replaced with a serine residue. In addition, in each pair, a KpnI recognition site has been introduced by converting GGAACA to GGTACC, and an SspI recognition site by converting AACATT to AATATT.

Following protective group elimination, a 64/100 portion of each synthesized oligonucleotide was purified by 12% acrylamide-urea gel electrophoresis. As a result, 15.9 μg of DNA-1, 22.0 μg of DNA-2, 19.0 μg of DNA-3, 21.1 μg of DNA-4, 8.8 μg of DNA-5 and 12.1

μg of DNA-6 were obtained each as a single-stranded DNA.

(3) Construction of pHR21, pHR23 and pHR26 pTT03 was digested with ClaI and a linearized 3.9 kb fragment was isolated and purified by agarose gel electrophoresis. This fragment was terminally dephosphorylated with calf intestine alkaline phosphatase. Separately, the oligonucleotides DNA-1 and DNA-2 synthesized as described above were subjected to kination and then to annealing, followed by ligation for joining to the dephosphorylated 3.9 kb fragment. A plasmid, which gave a 800 bp DNA fragment upon digestion with HindIII and ClaI, was named pHR21. Screening of 12 transformants gave 6 transformants harboring pHR21. Similarly, a plasmid, pHR23, containing a synthetic DNA (DNA-3 and DNA-4) coding for a PUK variant with an asparagine residue substituting for the 24-position thyrosine residue of PUK and a plasmid, pHR26, containing a synthetic DNA (DNA-5 and DNA-6) coding for a PUK variant with a serine residue substituting for the 29-position histidine residue were constructed.

In the case of pHR23, 8 out of 12 transformants were transformants harboring the desired plasmid and, in the case of pHR26, 6 out of 12 transformants were the desired transformants. The synthetic DNA portion in each plasmid was also confirmed by base sequence determination.

(4) Construction of pHR22 pHR24 and pHR27

Since pHR21, pHR23 and pHR26 have a DNA sequence coding for the first (serine) to 44th (isoleucine) residues of PUK, a DNA coding for the C-terminal side beginning with the 45-position asparagine residue was joined thereto for constructing pHR22, pHR24 and pHR27, respectively.

pUH7 was digested with ClaI and a 4.2 kb DNA fragment was isolated and purified by agarose gel electrophoresis. This fragment was dephosphorylated with calf intestine alkaline phosphatase and the digest was ligated to the 800 bp DNA fragment obtained by HindIII-ClaI digestion of pHR21 by utilizing the ClaI recognition site. Then, the HindIII recognition site and the ClaI recognition site (another end) were each rendered blunt with T4 DNA polymerase and ligation was again performed. Twenty-four transformants were subjected to preliminary screening using the size of the resulting circular plasmid as an index. Thus, comparison was made with a circular plasmid (pUH7) smaller by 100 bp than the desired plasmid. As a result, the plasmids in 5 out of the 24 transformants had the desired size. In this construction process, it was possible that the HindII-ClaI fragment be inserted in the reverse direction. Therefore, plasmids giving a 900-bp DNA fragment upon KpnI digestion were then screened out. As a result, 4 out of the 5 plasmids were found to be the desired one. An *Escherichia coli* strain harboring this plasmid pHR22 has been deposited at the Institute for Fermentation, Osaka (17-85 2-chome, Juso-Honmachi, Yodogawa-ku, Osaka, Japan) since Apr. 28, 1989 under the designation *Escherichia coli* HB101/pHR22 (deposit number IFO 14871).

pHR24 and pHR27 were constructed in the same manner. In both pHR24 and pHR27, only one of 24 plasmids screened was the desired plasmid.

(5) Introduction of expression vector into CHO cells

The three human PUK variant expression vectors pHR22, pHR24, pHR27 were introduced into CHO K1 cells.

CHO K1 cells ($5 \times 10^6$ cells) in the logarithmic growth phase were cotransfected with the human PUK variant expression plasmid pHR22 (10 μg or 100 μg) and the plasmid pSV-G1-Neo (0.13 μg; EP-A-154272) to serve as a selective marker by the electroporation method. The cells were suspended in 50 ml of Ham's F12 medium Nissui Pharmaceutical) supplemented with 10% fetal calf serum (MH01, Mitsubishi Kasei) and the suspension was distributed in 100-μl portions into wells of 96-well microplates. After incubation at 37° C. for 48 hours, G418 was added in a final concentration of 400 μg/ml. Thereafter, exchange of the selective medium was performed at 3- or 4-day intervals. When cells became almost confluent, the culture supernatant was assayed for PUK activity. Assuming that the human PUK activity of a variant in the culture supernatant was correlated with the activity of natural urokinase (UK), three days after medium exchange the supernatant was collected and assayed for plasminogen activator (PA) activity by the fibrin agar plate method with a standard UK as a reference. Cell strains that had produced not less than 1 IU/ml of the human PUK variant were selected and cultured on a large scale i.e., in 10 cm dishes, and activity assay was again carried out. pHR24 (10 μg or 100 μg) and pHR27 (10 μg or 100 μg) were also introduced into the same cells and the cell culture was carried out in the same manner. The results of the transfection are shown in Table 13.

TABLE 13

Transfection of CHO K1 cells with three human PUK variant expression plasmids; transduction efficiency and frequency of appearance of human PUK variant-producing strains

| Expression plasmid | Transduction efficiency[a] | Number of human PUK variant-producing clones/number of G-418 resistant clones |
|---|---|---|
| pHR22/10 μg | $1.0 \times 10^{-4}$ | 9/49 (18%) |
| pHR24/10 μg | $1.3 \times 10^{-4}$ | 7/59 (12%) |
| pHR27/10 μg | $0.9 \times 10^{-4}$ | 2/43 (5%) |
| pHR22/100 μg | $0.34 \times 10^{-4}$ | 9/16 (56%) |
| pHR24/100 μg | $0.41 \times 10^{-4}$ | 13/19 (68%) |
| pHR27/100 μg | $0.22 \times 10^{-4}$ | 0/10 (0%) |

[a]The value obtained by dividing the number G-418 resistant clones by the number of CHO K1 cells was converted to a value per microgram of pSV-G1-neo. Since 5 × 10⁶ cells were suspended in 50 ml and distributed in 0.1-ml portions into 360 wells, the number of CHO K1 cells used amounted to $3.6 \times 10^6$.

When 10 μg of each expression vector was used for the transduction, the transduction efficiency amounted to 0.9 to $1.3 \times 10^{-4}$ and there were no significant differences in the efficiency among the plasmids used. When the plasmids were used for transduction each in an amount of 100 μg, the efficiency values were 0.2 to $0.4 \times 10^{-4}$ and showed no significant differences. However, when the plasmids were used in an amount of 10 μg, the transduction efficiency was 3 to 4 times higher as compares with the cases where the plasmids were used in an amount of 100 μg.

When incorporated into cells, pSV-G1-neo used for the cotransfection gives G-418 resistance to the cells. When an equimolar amount of pSV-G1-neo is introduced into the same number of cells, the transduction efficiency must be constant. Since, however, as mentioned above, there was a great (10 times) difference in the quantity of the coexisting plasmid and the coexisting plasmid was present in a mole ratio of 80 or 800 to 1 relative to pSV-G1-neo when a pulsating 1,000-V electric field was applied, the expression plasmid might possibly have prevented pSV-G1-neo from being introduced into the cells. Thus, it is thought that the proportion of pSV-G1-neo relative to the coexisting plasmid might have caused the difference in transduction efficiency.

On the other hand, it is seen that the proportion of human PUK variant-producing clones among G-418 resistant clones was higher when 100 μg of the expression plasmid was used. That is the molar proportion of the expression plasmid was higher than when 10 μg of the expression plasmid was used. With the exception of pHR27, human PUK variant-producing strains can be obtained with a frequency of 10 to 20% through the use of 10 μg of the expression plasmid or with a frequency as high as 50% or more through the use of 100 μg of the expression plasmid. In addition, it has become possible to isolate high production strains. The human PUK variant-producing clones obtained by transduction show a distribution according to Table 14 when grouped in terms of production capacity.

TABLE 14

Distribution of cells transfected with human PUK variant expression plasmids as grouped in terms of production on 96-well plates

| Plasmid introduced | Number of clones in a specific range of PA activity (IU/ml) that the clones show | | | | |
|---|---|---|---|---|---|
| | 0 | 0-5 | 5-20 | 20-50 | 50- |
| pHR22/10 μg | 40 | 5 | 3 | 1 | 0 |
| pHR24/10 μg | 52 | 5 | 2 | 0 | 0 |
| pHR27/10 μg | 41 | 2 | 0 | 0 | 0 |
| pHR22/100 μg | 7 | 1 | 7 | 1 | 0 |
| pHR24/100 μg | 6 | 9 | 4 | 0 | 1 |
| pHR27/100 μg | 10 | 0 | 0 | 0 | 0 |

Since, however, medium exchange cannot be performed to a sufficient extent and the number of cells tends to vary widely under the growth conditions of 96-well plates, clones showing a production of 1 IU/ml or more were cultured on a larger scale, namely in 10-cm dishes, and an activity comparison was made. The results are shown in Table 15.

TABLE 15

Distribution of cells transfected with human PUK variant expression plasmids as grouped in terms of production in 10 cm dishes

| Plasmid introduced | Number of clones in a specific range of PA activity (IU/ml) that the clones show | | | |
|---|---|---|---|---|
| | 0-5 | 5-20 | 20-50 | 50- |
| pHR22/10 μg | 2 | 1 | 2 | 1 |
| pHR24/10 μg | 1 | 4 | 0 | 0 |

TABLE 15-continued

Distribution of cells transfected with human PUK variant expression plasmids as grouped in terms of production in 10 cm dishes

| Plasmid introduced | Number of clones in a specific range of PA activity (IU/ml) that the clones show | | | |
|---|---|---|---|---|
| | 0-5 | 5-20 | 20-50 | 50- |
| pHR27/10 μg | 0 | 0 | 1 | 0 |
| pHR22/100 μg | 0 | 5 | 3 | 0 |
| pHR24/100 μg | 3 | 7 | 3 | 1 |

A comparison of Table 13 to Table 14, shows that the PA activity of each clone is in general higher in Table 14. Based on this, it may be concluded that the growth conditions in 10-cm dishes are more favorable to human PUK variant production than those on 96-well plates.

Clones showing a human PUK variant production of not less than 20 IU/ml in 10-cm dishes are shown in Table 16 together with the activity data obtained when they were cultured on 96-well plates.

TABLE 16

Activities of human PUK variants in 10 cm dishes

| Clone | Activity (IU/ml) | |
|---|---|---|
| | 10 cm dish | 96 well plate |
| pHR22(10)213 | 26 | 6 |
| pHR22(10)122 | 30 | 6 |
| pHR22(10)253 | 80 | 44 |
| pHR22(100)201 | 33 | 21 |
| pHR22(100)112 | 24 | 13 |
| pHR22(100)211 | 42 | 11 |
| pHR22(100)611 | 35 | 13 |
| pHR24(100)402 | 24 | 11 |
| pHR24(100)311 | 42 | 12 |
| pHR24(100)413 | 38 | 7 |
| pHR24(100)422 | 336 | 111 |
| pHR27(10)121 | 37 | 3 |

In this case, too, it can be seen that the growth conditions in 10-cm dishes are preferable.

The introduction of the respective expression plasmids into CHO K1 cells gave the following high production clones: a 80 IU/ml clone upon introduction of 10 μg of pHR22; a 340 IU/ml clone upon introduction of 100 μg of pHR24; and a 37 IU/ml clone upon introduction of 10 μg of pHR27.

EXAMPLE 7

(1) Synthesis of oligonucleotides

Four single-stranded DNAs (SD7, SD8, SD9, and SD10) were prepared using an automatic DNA synthesizer (Applied Biosystems model 381A). Their base sequences are shown below. The numbering of the amino acid residues corresponds to that of human PUK (FIG. 1).

```
          9   10   33   34   35                    40                        45
         Ser  Asn  Cys  Pro  Lys  Lys  Phe  Gly  Gly  Gln  His  Cys  Glu    Ile  Asp

SD7  5'- CG  AAC  TGC  CCA  AAG  AAA  TTC  GGA  GGG  CAG  CAC  TGT  GAA      AT-3'  (40 bases)
SD8  3'-     TTG  ACG  GGT  TTC  TTT  AAG  CCT  CCC  GTC  GTG  ACA  CTT    TAGC-5'  (40 bases)

9   10   11                    15                        20                        25
         Ser  Asn  Cys  Asp  Cys  Leu  Asn  Gly  Gly  Thr  Cys  Val  Ser  Asn  Lys  Tyr  Phe  Ser  Asn

SD9  5'- CG  AAC  TGT  GAC  TGT  CTA  AAT GGA  GGT  ACC  TGT  GTG  TCC  AAC  AAG  TAC  TTC  TCC  AAC
SD10 3'-     TTG  ACA  CTG  ACA  GAT  TTA  CCT  CCA  TGG  ACA  CAC  AGG  TTG  TTC  ATG  AAG  AGG  TTG
```

```
        30           32  43  44  45
Ile   His  Trp  Cys  Asn Glu Ile Asp
```

ATT CAC TGG TGC AAC GAA AT-3' (76 bases)
TAA GTG ACC ACG TTG CTT TAG C-5' (76 bases)

Each DNA synthesized was eluted from the column with ammonia. dried by heating at 55° C. for 20 hours, and dissolved in distilled water. At this point, the yields were as follows: SD7, 1.75 mg; SD8, 1.61 mg; SD9, 2.81 mg: and SD10, 2.61 mg. A 1/5 portion of each DNA was purified on modified polyacrylamide. The final yields were as follows: SD7, 10.2 µg: SD8, 9.01 µg; SD9, 7.7 µg; and SD10, 7.0 µg. The two pairs, SD7-SD8 and SD9-SD10 were subjected to kination and then to annealing and the annealing products were used for the plasmid construction mentioned below.

Figure 14:
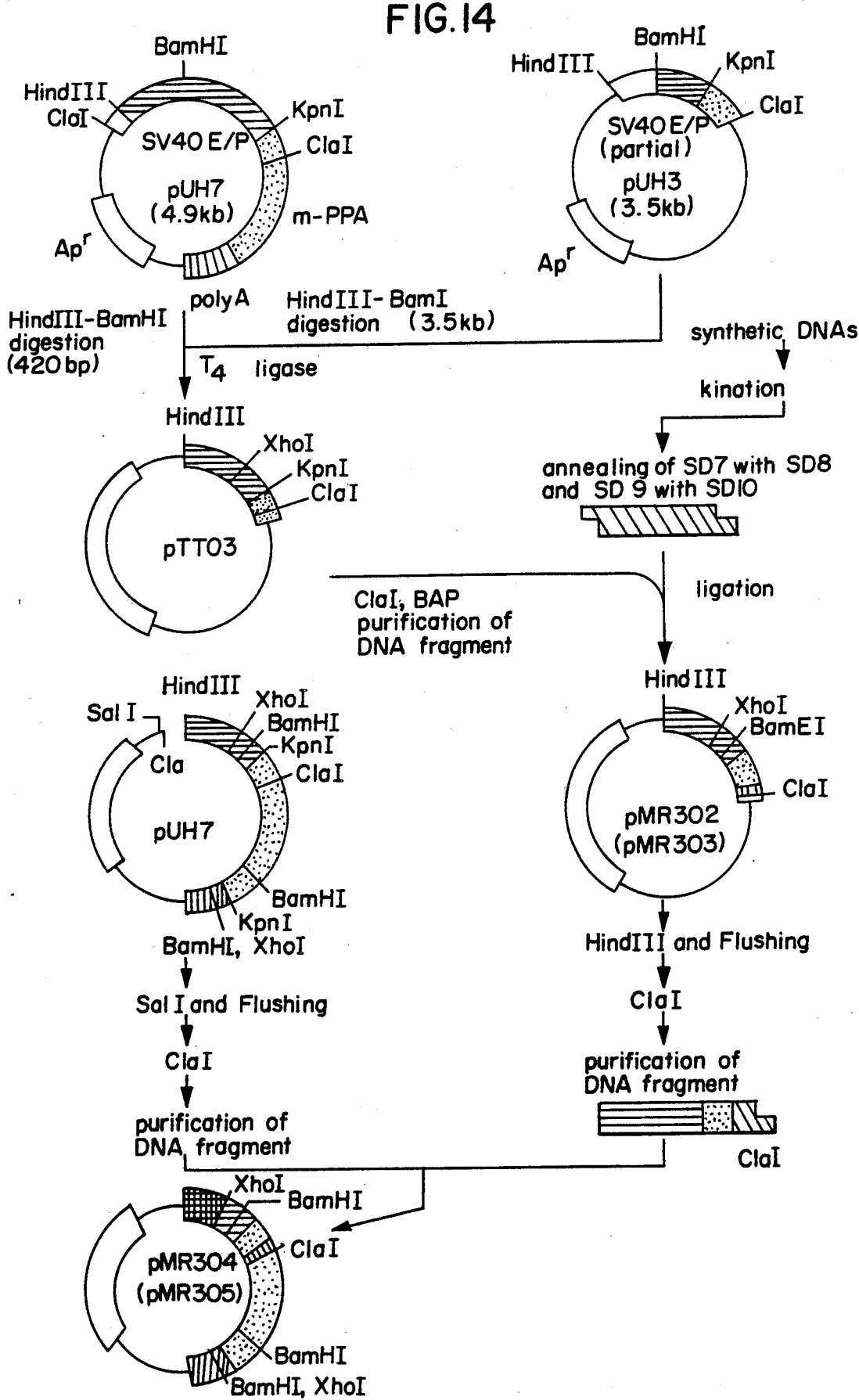
FIG. 14 shows a process for preparing plasmids pMR304 and pMR305.

(2) Construction of pMR304 and pMR305 (cf. FIG. 14)

An expression vector for a human PUK variant deficient in the first and second loops of the EGF domain was named pMR304 (an *Escherichia coli* strain harboring the vector has been deposited, since Apr. 28, 1989. with the Institute for Fermentation, Osaka, 17-85, Juso-Honmachi 2-chome, Yodogawaku, Osaka, Japan, under the designation *Escherichia coli* HB101/pMR304 and under the deposit number IFO 14872). An expression vector for a human PUK variant deficient in the third loop was named pMR305 (an *Escherichia coli* strain harboring the vector has been deposited since Oct. 25, 1989 with the Institute for Fermentation, Osaka, under the designation *Escherichia coli* HB101/pMR305 and under the deposit number IFO 14964). Intermediates for constructing these vectors were named pMR302 and pMR303, respectively. The synthetic DNAs SD7 and SD8 were used in constructing pMR302 while SD9 and SD10 were used in constructing pMR303.

pTT03 was digested with ClaI and dephosphorylated with BAP, and the resulting linear DNA (3.9 kb) was purified by the DEAE paper method. This was ligated to the double-stranded DNA resulting from annealing of each pair of synthetic DNAs as obtained above and the ligation mixture was used to transform JM109 competent cells. Digestion with BamHI and ClaI gives a DNA fragment about 300 bp in size in the case of pMR302 or a DNA fragment about 340 bp in size in the case of pMR303. Screening was made using this as an index and 8 transformant clones were obtained for each of pMR302 and pMR303. The base sequences of the inserted DNA portions, namely the synthetic DNA portions, were confirmed by double-stranded DNA sequencing by the dideoxy method. Plasmid preparation from clones identified with respect to the base sequences gave 582 µg of pMR302 and 522 µg of pMR303.

pMR302 and pMR303 were each digested with HindIII, then rendered blunt-ended using T4 DNA polymerase, and digested with ClaI. A pMR302-derived 780-bp DNA fragment were purified on a DEAE paper.

pUH7 was digested with SalI and rendered blunt-ended with T4 DNA polymerase. After further digestion with ClaI, a 4.0-kbp DNA fragment was purified by the DEAE paper method. This DNA fragment was ligated to the DNA fragment excised from pMR302 or pMR303 and the ligation mixture was used to transform JM109 competent cells. Each desired plasmid must be cleaved with ClaI at one site only and digestion with both the restriction enzymes ClaI and XhoI must give three DNA fragments 4.9 kg, 1.4 kb and about 360 bp in size in the case of pMR304 or, in the case of pMR305, three DNA fragments 4.9 kb, 1.4 kb and about 390 bp in size. With these as indices, screening was performed and the desired plasmids were prepared. Thus were obtained 384 µg of pMR304 and 408 µg of pMR305.

(3) Introduction into CHO cells of expression vector for human PUK variants deficient in part of EGF domain The two human PUK variant expression vectors pMR304 and pMR305 were introduced into CHO K1 cells.

Cell culture medium, serum and reagent

The following medium constituents were used for the cell culture: Ham's F12 (Nissui Pharmaceutical); fetal calf serum (Mitsubishi Kasei Corp., hereinafter abbreviated as "FCS"); Hanks' solution (Nissui Pharmaceutical); lilacillin (synthetic penicillin; Takeda Chemical Industries), streptomycin (Meiji Seika); trypsin (Boehringer Mannheim); and G418 (Sigma). Ham's F12 (hereinafter referred to as "F12 medium") containing 100 mg/liter of lilacillin and 10 mg/liter of streptomycin was prepared. filter sterilized, distributed in 1-liter portions, and stored at 4° C.

Activity assay of human PUK variants

It was assumed that the human PUK activity of a variant in the culture supernatant was correlated with the activity of natural urokinase (UK). Three days after medium exchange, the supernatant was collected and assayed for plasminogen activator (PA) activity by the fibrin agar plate method (Arch. Biochem., 40, 346–351 (1952)) with a standard UK (Green Cross Corp.) as a reference.

DNA introduction into cells (by electroporation)

CHO K1 cells in the logarithmic growth phase were dispersed by trypsin treatment, washed twice with Hanks' solution, and suspended in Hanks' solution at a cell density of $10^7$ cells/ml. In a cuvette fitted with electrodes, 0.5 ml of this cell suspension was mixed with 100 ng of pSV-G1-Neo (EP-A-154272; FIG. 4) and 10 µg or 100 µg of the plasmid in question. A 1,000-volt pulse electric field was applied two times and the suspension was allowed to stand for 5 minutes. This cell suspension was diluted with 50 ml of F12 medium supplemented with 10% FCS and the dilution was inoculated in 100-µl portions into a 96-well microplate.

Selection of G418-resistant strains

After electroporation, the dilution was incubated at 37° C. for 48 hours and F12 medium containing 10% FCS and 800 µg/ml of G418 was distributed in 100-µl portions into the wells. Thereafter, medium exchange was performed two times a week using F12 medium containing 400 µg/ml of G418 and 10% FCS.

Screening for high productivity strains

After about 2 weeks, colonies at a grown stage were assayed for PA activity and those showing a high activity were cultured on a larger scale. These were inoculated into 10-cm culture dishes at an inoculum size of $1 \times 10^6$ cells per dish. After 3 days, the cells were counted and the PA activity per unit number of cells was calculated.

Introduction of pMR304 and pMR305 into cells and isolation of high expression strains for human PUK variants CHO K1 cells in the logarithmic growth phase were cotransfected with pMR304 or pMR305 and pSV-G1-Neo by the electroporation method. After about 2 weeks, formation of G418-resistant colonies began. The PA activity values for these colonies as determined on a 96-well microplate scale are shown in Table 17 and Table 18.

TABLE 17

Distribution of CHO K1 clones transfected with pMR304 as grouped in terms of PA Activity

| | PA activity (IU/ml) | | | | | | |
|---|---|---|---|---|---|---|---|
| | 0 | <5 | <10 | <15 | <20 | >20 | Total |
| After introduction of 10 μg | 7 | 1 | 2 | 0 | 0 | 0 | 10 |
| After introduction of 100 μg | 6 | 1 | 1 | 2 | 0 | 1 | 11 |
| Total | 13 | 2 | 3 | 2 | 0 | 1 | 21 |

TABLE 18

Distribution of CHO K1 clones transfected with pMR305 as grouped in terms of PA activity

| | PA activity (IU/ml) | | | | | | |
|---|---|---|---|---|---|---|---|
| | 0 | <5 | <10 | <15 | <20 | >20 | Total |
| After introduction of 10 μg | 21 | 2 | 1 | 0 | 0 | 0 | 24 |
| After introduction of 100 μg | 1 | 0 | 1 | 0 | 1 | 0 | 2 |
| Total | 22 | 2 | 1 | 0 | 1 | 0 | 26 |

Among these clones, those that gave the highest PA activity values were cultured on a larger scale in an attempt to isolate high productivity strains. The PA activity data obtained upon larger scale culture in 10-cm culture dishes at an inoculum size of $10^6$ cells per dish as well the data for 96-well plate culture are shown in Table 19.

TABLE 19

PA activities attained upon larger scale culture of strains showing highest activities on 96-well plate

| Plasmids | Clone | PA activity (IU/ml/3 days) 96-well | PA activity (IU/ml/3 days) 10-cm dish | Number of cells in 10-cm dish[a] | PA activity (IU/$10^5$/ 3 days) |
|---|---|---|---|---|---|
| pMR304 | 10B4 | 91.22 | 85.57 | $3.08 \times 10^6$ | 28.8 |
| pMR305 | 5B7 | 19.09 | 45.1[40.8] | [$7.24 \times 10^6$] | [5.7] |

Note:
[a]Number of cells 3 days after inoculation with cells. The values in square brackets were obtained after cell storage in the frozen state, followed by thawing.

EXAMPLE 8

(1) Purification of human PUK variants

CHO K1 cells transfected with pHR22, CHO K1 cells transfected with pHR24 and CHO K1 cells transfected with pHR27 were used.

The culture supernatants of the above three transfectants were applied to a column of Chelating Sepharose 6B (Pharmacia) carrying zinc ions for adsorption of human PUK variant and the column was washed with 20 mM Tris-HCl buffer (pH 7.5) containing 10 KIU/ml aprotinin, and 1M sodium chloride, followed by elution with 20 mM Tris-HCl buffer (pH 7.5) containing 50 mM imidazole, 10 KIU/ml aprotinin and 1M sodium chloride.

The resulting eluate was applied to a column of benzamidine-Sepharose 6B (Pharmicia) equilibrated with 0.1M phosphate buffer (pH 6.5) containing 0.5M sodium chloride. Then, the column washed with 0.1M phosphate buffer (pH 6.5) containing 10 KIU/ml aprotinin and 0.5M sodium chloride and the fraction passed through the column was collected.

Formyl-Cellulofine (Pharmacia) to which altn-urine-derived urokinas antibody was bonded was equilibrated with 0.1M phosphate buffer (pH 6.5) containing 0.5M sodium chloride. The above-obtained fraction was applied thereto, the column was washed with the same buffer, and elution carried out with 0.2M glycine-HCl buffer (pH 2.5) containing 0.5M sodium chloride.

The eluate was further applied to a column of benzamidine-Sepharose 6B and the fraction that passed through the column collected.

This fraction was dialyzed against 0.1M phosphate buffer (pH 6.2) to obtain purified human PUK variant.

The thus-obtained human PUK variants derived from pHR22, pHR24 and pHR27 are hereinafter referred to as Ser24-PUK, Asn24-PUK and Ser29-PUK, respectively. These three human PUK variants showed a specific activity of 150,000 IU/mg protein when treated with plasmin.

(2) Properties of human PUK variants a) Molecular weight

A molecular weight for human PUK variants was determined by SDS-polyacrylamide gel electrophoresis (SDS-PAGE) in accordance with the method of Laemmli (Nature, 227, 680 (1970)).

189-350 IU of each human PUK variant was boiled at 100° C. for 10 minutes in a reducing solution containing 2% 2-mercaptoethanol. 2% SDS, 10% glycerol, and 50 mM Tris-HCl buffer (pH 6.8). Each reaction mixture was applied onto a 10 to 20% gradient gel (Daiichi Kagaku Yakuhin) and electrophoresis was carried out at a constant current of 30 mA for 2 hours. The following molecular weight markers were used: phosphorylase b, 94,000; bovine serum albumin, 67,000; ovalbumin, 43,000; carbonic anhydrase, 30,000; trypsin inhibitor, 20,100; and α-lactalbumin, 14,400 (Pharmacia).

After electrophoresis, the gel were stained by Coomassie Brillian Blue R-250.

As a result bands of Ser24-PUK and Asn24-PUK were found at 50KD and 52KD, respectively. With respect to Ser29-PUK, a smear-like band was observed at approximately 50 KD. Since the position of the bands of human PUK variants did not change under either reducing conditions or nonreducing conditions, it is suggested that human PUK variants according to the present invention have a single-stranded molecular structure.

b) Enzyme kinetics

Glt-Gly-Arg-MCA (hereinafter abbreviated as MCA), 7-amino-A-methyl-Coumarin (hereinafter abbreviated as AMC) were commercially available from the Peptide Research Institute. The UK standard and plasmin used were products of The Green Cross Corporation.

The initial reaction rate was determined in the following manner.

A 100 μl portion of a 200 μl/ml solution of each human PUK variant (Ser24-PUK, Asn24-PUK and Ser29-PUK) was mixed with 100 μl of a 0.2 cu/ml solution of plasmin. As a buffer solution for human PUK variants and plasmin, 0.1 M Tris-HCl buffer (pH 8.4) containing 0.1M NaCl and 10% gelatin was used. The resulting was incubated at 37° C for 10 minutes. Then, a 0.8 ml portion of 1.0, 0.5, 0.25, 0.125, or 0.625 mM solution of MCA previously maintained at 37° C. was added to the mixture. After further incubation at 37° C. for 3 minutes, 2 ml of a 15% acetic acid solution was added to the mixture to terminate the reaction. For comparison, naturally occurring human PUK (n-PUK; cf. EP-A-139447) was used. Fluorescence intensity of the resulting mixture was measured using a spectrophotofluorometer at an excitation wavelength of 370 nm and a fluorescence wavelength of 460 nm. The concentration of AMC produced by the enzyme reaction was calculated with the fluorescence intensity of 10 μM AMC as 100.

The kinetic constants, Km and Vmax, were calculated in accordance with the Lineweaver-Burk plot method (Segei, I.H. (1976) Biochemical Calculations, 2nd ed. John Wiley & Sons, Inc., New York). kcat was calculated by the following equation on the ground that 1 IU of UK corresponded to $1.33 \times 10^{-7}$ μmole.

$$kcat = \frac{Vmax}{1.33 \times 10^{-7}} \ (min.^{-1})$$

The kinetic constants of each human PUK variant are shown in Table 20.

TABLE 20

| Kinetic constant of human PUK variants | | | |
|---|---|---|---|
| Sample | KM (μM) | kcat × 10² (min.⁻¹) | kcat/Km |
| n-PUK | 355 | 84 | 2.4 |
| Ser24-PUK | 299 ± 30.1 | 81 ± 0 | 2.7 ± 0.3 |
| Asn24-PUK | 408 ± 73.9 | 104 ± 6 | 2.6 ± 0.3 |
| Ser29-PUK | 456 ± 115.1 | 100 ± 6 | 2.4 ± 0.7 |

Note:
The values shown in Table 6 are the mean ± standard deviation. The measurement was carried out once in the case of n-PUK and twice in the case of human PUK variants.

As shown in Table 20, there is no significant difference in kinetic constant between human PUK variants and natural human PUK.

c) Half-life in Blood

Half-lives in blood of n-PUK (natural: naturally occurring PUK derived from HGK cell; cf. EP-A-139447), n-PUK (recombinant: PUK produced by CHO K1 cells transformed with pSV-G1-preUK), $\Delta E_1 E_2$-$\Delta E_3$-PUK (human PUK variant deficient in the entire EGF domain), Ser24-PUK, Asn24-PUK and Ser29-PUK were examined.

The above six samples were labeled with $^{125}I$ using the lactoperoxidase Enxymobeads (BIO-RAD) method. The radiochemical specific activity of $^{125}I$-PUK thus obtained was calculated from protein content and radioactivity determined from absorbance at 280 nm. As a result, the specific activity of each sample fell within the range from 11000 to 56000 cpm/IU.

The sample solution was adjusted with physiological saline so as to given a PUK concentration of $2 \times 10^4$ IU/ml (human albumin concentration: 5%) and was administered to WISTER male rats (6-week-old) in a dose of 1 ml/kg through the tail vein.

Rats were anesthetized with 35 mg/kg i.m. of ketamine hydrochloride (trade name: Ketalar® produced by Sankyo) and 1.5 g/kg i.m. of urethane (Nakarai Chemical) and fixed on the back. An atom venous catheter (3Fr) filled with a 3.8% solution of sodium citrate (The Green Cross Corporation) was inserted into left carotid artery. 1, 2, 3, 5, 7, 10, 15, and 20 minutes after the administration of samples, blood was collected from each rat using JMS 1 ml-volume disposable syringe containing 30 μl of a 3.8% solution of sodium citrate blood up to the scale of 330 μl (300 μl in terms of blood). The sucked blood was shaken in the syringe and the whole sucked blood measured for radioactivity using a γ-counter (COMPUGAMMA 1282 model, LKB WALLAC). After radioactivity of the blood was measured, the whole blood was centrifuged at 3000 rpm for 10 minutes to obtain 100 μl of plasma. The thus-obtained plasma was rapidly frozen on dry ice and stored at −20° C.

A time course of radioactivity of blood was measured and calculated in terms of percentage of dose. A half-life in blood was calculated using commercially available software.

A half-life in blood (T1/2α) is shown in Table 21.

TABLE 21

| | T1/2α (min.) |
|---|---|
| Sample | Radioactivity |
| n-PUK (Natural type) | 2.49 ± 0.17 |
| n-PUK (recombinant) | 2.25 ± 0.54 |
| $\Delta E_1 E_2 E_3$-PUK | 5.65 ± 0.66* |
| Ser24-PUK | 5.11 ± 0.10* |
| Asn24-PUK | 6.84 ± 1.14* |
| Ser29-PUK | 5.59 ± 0.99* |

Note:
*Each value means the mean ± standard deviation (n-8).

As shown in Table 21, there is a significant difference in half-life in blood such that human PUK variants according to the present invention show a half-life (in terms of radioactivity) about two to three times longer than n-PUKs (p<0.05). Ser24-PUK, Asn24-PUK, and Ser29-PUK showed T1/2α comparable to that of $\Delta E_1 E_2 E_3$-PUK.

EXAMPLE 9 pMR304-derived human PUK variant (hereinafter $\Delta E_1 E_2$-PUK) and pMR305-derived human PUK variant (hereinafter $\Delta E_3$-PUK) were isolated and purified in the same manner as in Example 8.

Purified $\Delta E_1 E_2$-PUK and $\Delta E_3$-PUK both showed a specific activity of 150,000 IU/mg of protein when treated with plasmin.

Properties of each human PUK variant were determined in accordance with the methods described in Example 8.

Molecular weight

As a result of electrophoresis, bands of $\Delta E_1E_2$-PUK and $\Delta E_3$-PUK were found at 48K and 49K, respectively. This result suggested that human PUK variants according to the present invention have a single-stranded molecular structure.

Enzyme kinetic

The kinetic constants of each human PUK variant are shown in Table 22.

TABLE 22

| Kinetic constant of human PUK variants | | | |
|---|---|---|---|
| Sample | KM (μM) | kcat × 10² | kcat/Km |
| n-PUK | 355 | 84 | 2.4 |
| $\Delta E_1E_2$-PUK | 340 + 2.4 | 91 + 1 | 2.7 + 0.2 |
| $\Delta E_3$-PUK | 409 + 12.1 | 101 + 13 | 2.5 + 0.2 |

Note:
The value shown in Table 22 is the mean ± standard deviation. The measurement was carried out once in the case of n-PUK and twice in the case of human PUK variants.

As shown in Table 22, there is no significant difference in kinetic constant between human PUK variants and natural human PUK.

Half-life in Blood

The following samples were tested.
a) n-PUK (natural): naturally occurring PUK derived from HGK cells (cf. EP-A-139447).
b) n-PUK (recombinant): PUK produced by CHO K1 cells transformed with pSV-G1-preUK.
c) $\Delta E_1E_2E_3$-PUK: human PUK variant deficient in the entire EGF domain.
d) $\Delta E_1E_2$-PUK: human PUK variant deficient in the first loop and the second loop of the EGF domain.
e) $\Delta E_3$-PUK: human PUK variant deficient in the third loop of the EGF domain.

A half-life in blood (T1/2α) is shown in Table 23.

TABLE 23

| Sample | T1/2α (min.) Radioactivity |
|---|---|
| n-PUK (Natural type) | 2.49 ± 0.17 |
| n-PUK (recombinant) | 2.25 ± 0.54 |
| $\Delta E_1E_2E_3$-PUK | 5.65 ± 0.66 |
| $\Delta E_1E_2$-PUK | 6.33 ± 1.00 |
| $\Delta E_3$-PUK | 5.39 ± 0.86 |

Note:
Each value means the mean standard deviation (n = 8).

As shown in Table 23, there is a significant difference in half-life in blood such that human PUK variants according to the present invention show a half-life (in terms of radioactivity) about two to three times longer than n-PUKs ($p<0.05$). $\Delta E_1E_2$-PUK and $\Delta E3$-PUK showed T1/2α comparable to that of $\Delta E_1E_2E_3$-PUK.

In accordance with the present invention, it is possible to provide human PUK mutants of physiological significance as urokinase precursors. Said human PUK mutants have significantly prolonged half-lives as compared with known human PUK species and urokinase. Thus, the invention provides more ideal fibrinolytic enzymes which are expected to produce a beneficial effect in the field of medicine.

While the invention has been described in detail and with reference to specific embodiments thereof, it will be apparent to one skilled in the art that various changes and modifications can be made therein without departing from the spirit and scope thereof.

What is claimed is:
1. A human prourokinase mutant in which at least all of the epidermal growth factor domain which consists of Asn10 to Cys42 of said human prourokinase is absent and which has a longer blood half-life than naturally occurring human prourokinase while retaining prourokinase enzymatic activity.
2. The human prourokinase mutant as claimed in claim 1, wherein the region selected from the group consisting of
   (a) from asparagine (10) to cysteine (42);
   (b) from asparagine (10) to aspartic acid (45); and
   (c) from asparagine (10) to threonine (49);
is deleted.

* * * * *